US011781035B2

(12) United States Patent
Taton et al.

(10) Patent No.: US 11,781,035 B2
(45) Date of Patent: *Oct. 10, 2023

(54) POLYUREA COPOLYMER COATING COMPOSITIONS AND METHODS

(71) Applicant: Innovative Surface Technologies, Inc., St. Paul, MN (US)

(72) Inventors: Kristin Taton, Little Canada, MN (US); Daniel Guire, Hopkins, MN (US); Nathaniel Olson, Minneapolis, MN (US); Eric Guire, St. Paul, MN (US); Patrick Guire, Hopkins, MN (US)

(73) Assignee: Innovative Surface Technologies, Inc., St. Paul, MN (US)

( * ) Notice: Subject to any disclaimer, the term of this patent is extended or adjusted under 35 U.S.C. 154(b) by 496 days.

This patent is subject to a terminal disclaimer.

(21) Appl. No.: 16/771,285

(22) PCT Filed: Dec. 11, 2018

(86) PCT No.: PCT/US2018/064983
§ 371 (c)(1),
(2) Date: Jun. 10, 2020

(87) PCT Pub. No.: WO2019/118483
PCT Pub. Date: Jun. 20, 2019

(65) Prior Publication Data
US 2020/0377756 A1 Dec. 3, 2020

Related U.S. Application Data

(60) Provisional application No. 62/703,412, filed on Jul. 25, 2018, provisional application No. 62/597,148, filed on Dec. 11, 2017.

(51) Int. Cl.
| | |
|---|---|
| *C08G 18/32* | (2006.01) |
| *C09D 175/02* | (2006.01) |
| *A61B 5/00* | (2006.01) |
| *B05D 1/02* | (2006.01) |
| *B05D 1/18* | (2006.01) |
| *C08G 18/50* | (2006.01) |
| *C08G 18/66* | (2006.01) |
| *C08G 18/73* | (2006.01) |
| *C08G 18/75* | (2006.01) |
| *C09D 5/16* | (2006.01) |

(52) U.S. Cl.
CPC .......... *C09D 175/02* (2013.01); *A61B 5/6846* (2013.01); *B05D 1/02* (2013.01); *B05D 1/18* (2013.01); *C08G 18/325* (2013.01); *C08G 18/3228* (2013.01); *C08G 18/5024* (2013.01); *C08G 18/6685* (2013.01); *C08G 18/73* (2013.01); *C08G 18/755* (2013.01); *C09D 5/1662* (2013.01)

(58) Field of Classification Search
CPC ........ A61B 5/6846; A61N 1/375; B05D 1/02; B05D 1/18; C08G 18/3228; C08G 18/324; C08G 18/3243; C08G 18/3246; C08G 18/325; C08G 18/5024; C08G 18/6685; C08G 18/73; C08G 18/755; C09D 5/1662; C09D 175/02
See application file for complete search history.

(56) References Cited

U.S. PATENT DOCUMENTS

| | | | |
|---|---|---|---|
| 2,852,494 | A | 9/1958 | Lehmann et al. |
| 4,045,510 | A | 8/1977 | Login |
| 4,442,280 | A | 4/1984 | Grogler et al. |
| 4,761,465 | A | 8/1988 | Speranza et al. |
| 5,162,388 | A | 11/1992 | Primeaux, II |
| 5,214,119 | A | 5/1993 | Leir et al. |
| 5,290,615 | A | 3/1994 | Tushaus et al. |
| 5,759,695 | A | 6/1998 | Primeaux, II |
| 5,786,439 | A | 7/1998 | Van Antwerp et al. |
| 5,792,554 | A | 8/1998 | Leir et al. |
| 5,856,420 | A | 1/1999 | Tucker et al. |
| 5,866,222 | A | 2/1999 | Seth et al. |
| 6,013,755 | A | 1/2000 | Primeaux, II et al. |
| 6,020,392 | A | 2/2000 | Kushner et al. |
| 6,166,093 | A | 12/2000 | Mougin et al. |
| 6,369,189 | B1 | 4/2002 | Naderhoff et al. |

(Continued)

FOREIGN PATENT DOCUMENTS

| | | |
|---|---|---|
| EP | 1183295 B1 | 10/2007 |
| WO | 2007006656 A1 | 1/2007 |

(Continued)

OTHER PUBLICATIONS

International Search Report for corresponding International Application No. PCT/US2018/064983, dated Mar. 14, 2019 (2 pages).
Huntsman Corporation,"Technical Bulletin, Huntsman Jeffamine® D-2000 amine," 2 pages (2006).
Extended European Search Report for corresponding European Patent Application No. EP 18 88 7262, dated Jul. 26, 2021 (3 pages).
Huntsman,"Technical Bulletin Jeffamine® ED-600 Polyetheramine," 2 pages (2007).
Hampton Research, "Jeffamine ED-2001 pH 7.0," 2 pages (2021).
Huntsman, "Technical Bulletin Jeffamine® ED-900 Polyetheramine," 2 pages (2007).

*Primary Examiner* — John M Cooney
(74) *Attorney, Agent, or Firm* — Resolute Legal PLLC

(57) ABSTRACT

Durable polyurea copolymer coatings can be applied to surfaces that come in contact with fluids, such as biological fluids, thereby passivating the surface. Polyurea copolymer coating compositions comprise a reaction product of (a) a diamine composition that includes a polyethylene glycol diamine, and optionally, a dipiperidyl alkane; and (b) a diisocyanate. Solutions containing polyurea copolymers, coated surfaces and methods are also described.

26 Claims, No Drawings

(56) References Cited

U.S. PATENT DOCUMENTS

| | | |
|---|---|---|
| 6,399,736 B1 | 6/2002 | Primeaux, II et al. |
| 6,462,162 B2 | 10/2002 | Van Antwerp et al. |
| 6,479,587 B1 | 11/2002 | Stockinger et al. |
| 6,605,684 B2 | 8/2003 | Primeaux, II et al. |
| 6,824,820 B1 | 11/2004 | Kinning et al. |
| 7,001,948 B2 | 2/2006 | Gupta et al. |
| 7,977,430 B2 | 7/2011 | Devlin et al. |
| 9,738,818 B2 | 8/2017 | Sherman et al. |
| 9,845,376 B2 | 12/2017 | Fedurco et al. |
| 2001/0008931 A1 | 7/2001 | Van Antwerp et al. |
| 2002/0040763 A1 | 4/2002 | Grenda et al. |
| 2003/0004265 A1 | 1/2003 | Gupta et al. |
| 2003/0105220 A1 | 6/2003 | Gupta et al. |
| 2005/0113549 A1 | 5/2005 | Devlin et al. |
| 2007/0158616 A1 | 7/2007 | Luo et al. |
| 2010/0247904 A1 | 9/2010 | Larson et al. |
| 2013/0331509 A1* | 12/2013 | Sharp .................. C08G 77/458 524/588 |
| 2015/0072154 A1 | 3/2015 | Sheth et al. |
| 2015/0259463 A1 | 9/2015 | Fedurco et al. |
| 2015/0374594 A1 | 12/2015 | Das et al. |
| 2017/0081435 A1 | 3/2017 | Wen et al. |
| 2017/0204289 A1 | 7/2017 | Kurtz et al. |
| 2017/0275523 A1 | 9/2017 | McCrary et al. |

FOREIGN PATENT DOCUMENTS

| | | |
|---|---|---|
| WO | 2013016158 A1 | 1/2013 |
| WO | 2016043584 A1 | 3/2016 |
| WO | 2019118487 A1 | 6/2019 |

* cited by examiner

POLYUREA COPOLYMER COATING COMPOSITIONS AND METHODS

This application is a Section 371 National Stage Application of International Application No. PCT/US2018/064983, filed Dec. 11, 2018 and published as WO 2019/118483 on Jun. 20, 2019, which claims priority from U.S. Provisional Application No. 62/597,148, filed Dec. 11, 2017 and U.S. Provisional Application No. 62/703,412, filed Jul. 25, 2018, the contents of which are incorporated herein in their entirety for all purposes.

GOVERNMENT INTERESTS

This invention was made with government support under Grant Nos. 2R44MH101958 and 1R43NS11907, awarded by the National Institutes of Health. The government has certain rights in the invention.

FIELD OF THE INVENTION

Polyurea copolymer coating compositions for application to surfaces, particularly surfaces that come in contact with biological fluids, such as medical devices and diagnostics, and/or surfaces that remain for extended periods of time in contact with water, such as water treatment or marine applications. Polyurea copolymers with components adherent to target surface and components for modulating interaction with its environment (e.g., liquids and solutes). The polyurea copolymers can provide a passivating surface, or a surface having desired properties. Articles are also described that include the coating compositions on a surface, as well as methods to coat surfaces.

BACKGROUND OF THE INVENTION

Polyurea is an extremely versatile compound and is well known for a wide variety of uses, such as adhesives, components of liquid pavement marking compositions, elastomerically coating or lining materials, sealants, elastomeric foams, contact lenses, and personal care compositions. Such diverse uses require significantly different formulations and reaction conditions.

BRIEF SUMMARY OF THE INVENTION

Polyurea copolymers, solutions and coating compositions including these polyurea copolymers, methods of providing a passivating surface using the polyurea copolymers, and coated surfaces are described herein. Polyurea copolymers include polyethylene glycol diamine and diisocyanate repeating units separated by urea linkages. In some implementations, the diisocyanate is present in a molar ratio with total diamines in a range of 2:1 to 1:2, or a range of 1.3:1 to 1:1.3, or a range of 1.2:1 to 1:1.2, or a range of 0.9:1 to 1.2:1. In some implementations, diisocyanate is present in an amount that is equal to, or greater than, the amount of total diamines in the polyurea copolymer.

Inventive polyurea copolymers can provide passivating surfaces to medical devices and diagnostics. The polyurea copolymers can exhibit improved properties as compared to other polymers used to passivate surfaces. In particular, inventive polyurea copolymers can be synthesized under relatively simple reaction conditions, the copolymers can be soluble in mild solvents (e.g., water, alcohol, alcohol-water mixtures, or buffer solutions), can be easily applied to a wide variety of surfaces, and are customizable for particular applications.

In some aspects, inventive polyurea copolymers can provide antifouling coating compositions that are suitable for use as coatings on articles immersed in or exposed to an aquatic environment (referred to herein as "aquatic articles"). Aquatic environments encompass natural or artificial systems such as lakes, rivers, fountains, ponds (e.g., fish ponds), canals, aquariums, aquaculture systems, water holding or conveying systems, water reservoirs, open drinking water systems, brackish water environments, waste water and oceans. In these aspects, inventive polyurea copolymers can be used in connection with man-made structures such as docks, ship and boat hulls, buoys, drilling platforms, oil production rigs, and pipes that are immersed in water that are prone to fouling by aquatic organisms such as green and brown algae, barnacles, mussels, and the like.

In some implementations, polyurea copolymers are provided that are pre-formed, fully polymerized, customizable polymers that are soluble in water, alcohol, alcohol-water mixtures, or buffer solutions. In this sense, inventive polyurea copolymers are provided wherein no further polymerization is required to provide the desired characteristics of solubility, passivity, durability, molecular weight, viscosity, and the ability to attach to a surface via physisorption. This is in contrast to prepolymers, which generally refer to a starting polymer that has been reacted to an intermediate molecular mass state, and that can be further polymerized by reactive groups to a fully cured state that has a molecular weight much higher than the starting polymer.

In some implementations, the pre-formed, fully polymerized, customizable polymers comprise linear copolymers, i.e., a continuous chain of repeat units (the copolymer backbone). In some aspects, inventive polyurea copolymers can have a relatively low molecular weight, for example, inventive polyurea copolymers can have an average molecular weight of 100,000 or less, or 90,000 or less, or 80,000 or less, or 70,000 or less, or 60,000 or less, or 50,000 or less, or 40,000 or less, or 30,000 or less, or 20,000 or less, or an average molecular weight in a range of about 5,000 to about 100,000, or about 5,000 to about 90,000, or about 5,000 to about 80,000, or about 5,000 to about 70,000, or about 5,000 to about 60,000, or about 5,000 to about 50,000, or about 5,000 to about 40,000, or about 5,000 to about 30,000, or about 5,000 to about 20,000, or about 10,000 to about 15,000. Use of difunctional monomers (diamines and diisocyanates) that have molecular weights in specified ranges can allow the user to control the molecular weight and linear architecture of the final, pre-formed copolymer. In some aspects, control of molecular weight can have an impact on solubility of the polyurea copolymer.

In some aspects, inventive polyurea copolymers do not include silicon (for example, in the form of siloxane and/or silane groups).

In a first aspect, a coating composition for a surface comprises a polyurea copolymer comprising a reaction product of:

(a) a diamine composition comprising a poly(ethylene glycol) diamine having a formula (I), (II), or a combination of diamines of formulae (I) and (II):

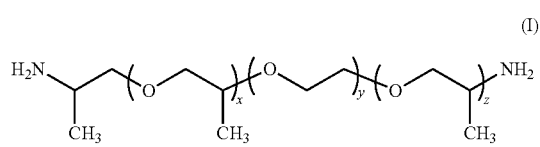

wherein y is an integer in the range of 2 to 40, and x+z is an integer in the range of 1 to 8; and

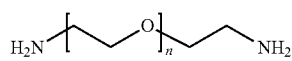
(II)

wherein n is an integer in the range of 1 to 500; and (b) a diisocyanate, wherein the diisocyanate is present in a molar ratio with total diamines in (a) in a range of 2:1 to 1:2, or a range of 1.3:1 to 1:1.3, or a range of 1.2:1 to 1:1.2, or in a range of 0.9:1 to 1.2:1. In some implementations, the diisocyanate is present in a 1:1 molar ratio, or in a 1.3:1 molar ratio, with total diamines in (a).

The diamine composition of (a) can include the following variations. In some implementations, the diamine composition of (a) comprises a secondary amine version of the poly(ethylene glycol) diamine of formula (I), in which the amine end-groups are reacted with a ketone (e.g., acetone) and reduced to create hindered secondary amine end groups represented by the following terminal structure represented by formula (III):

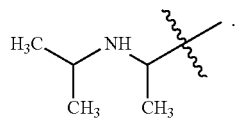
(III)

In these aspects, one reactive hydrogen on each end group provides for more selective reactivity. These embodiments can be useful for intermediate synthesis and intrinsically slower reactivity compared primary amines.

In some implementations, the diamine composition of (a) comprises a poly(propylene glycol) diamine having a formula (IV):

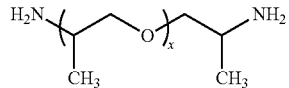
(IV)

wherein x is an integer in the range of 2 to 70; or
a poly(ethylene glycol) diamine having a formula (V):

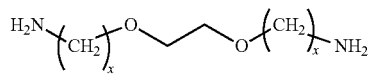
(V)

wherein x is 2 or 3.

Thus, in some aspects, the diamine composition of (a) can comprise any one of the diamines of Formulae (I) through (V), or a combination of any two or more of the diamines of Formulae (I) through (V). These diamine compositions are commercially available from Huntsman Corporation (The Woodlands, Tex., USA), under the JEFFAMINE® product lines, including JEFFAMINE® D, ED, EDR and SD series.

In some implementations, the coating composition can be a passivator. In other implementations, the coating composition can be a primer, wherein one or more additional coating layers are provided to the coating composition after it has been associated with a surface. In these aspects, additional coating layers can provide desirable properties to the coated surface, such as antimicrobial properties or the like.

Implementations can include any or all of the following features. The diamine composition can further include a dipiperidyl alkane, wherein the diamine combination comprises 20 to 99.9 molar percent of the polyethylene glycol and 0.1 to 80 molar percent of the dipiperidyl alkane. The polyethylene glycol diamine can have a molecular weight of about 100 to about 35,000, or about 100 to about 25,000, or about 100 to about 10,000, or about 500 to about 25,000, or about 500 to about 10,000, or about 500 to about 5,000.

Optionally, the diamine composition of (a) further comprises a dipiperidyl alkane, wherein the diamine composition comprises 20 to 99.9 molar percent of the polyethylene glycol and 0.1 to 80 molar percent of the dipiperidyl alkane. The dipiperidyl alkane can have a formula:

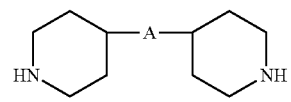
(VI)

where A is a C0 to C8 bivalent alkyl radical. In some aspects, the dipiperidyl alkane comprises dipiperidyl propane.

In some implementations, the diisocyanate has a formula:

$$OCN-B-NCO \quad (VII)$$

where B is a bivalent alkyl radical having 2 to 20 carbon atoms. The diisocyanate can be selected from hexane diisocyanate and isophorone diisocyanate.

In some aspects, the polyurea copolymer can comprise polyethylene glycol in amount of 25 to 95 weight percent, based on total weight of the polyurea copolymer.

It has been found that typical polyurea copolymers formed as described herein can include excess isocyanate at one or both end groups (terminal ends) of the copolymer. Over time, these isocyanate groups can covert to amines, typically through reaction with water. Optionally, this feature of the polyurea copolymers can be utilized to couple desired components to the polyurea copolymer, such as, for example, latent reactive groups, biomolecules, dyes and the like. Inclusion of latent reactive groups and/or biomolecules can provide customizable copolymers, wherein the end user can attach additional components based upon the ultimate use of the copolymers. In some implementations, latent reactive groups can be utilized to attach additional coating layers (such as topcoat layers) to a surface. In these instances, the polyurea copolymer coating layer can act as a priming layer for attachment of additional desired coating layers. In some aspects, latent reactive groups can provide improved durability of the copolymers, when applied to a surface.

Illustrative latent reactive groups include photoreactive, thermally reactive, and/or chemically reactive groups as discussed herein. Illustrative biomolecules include avidin (including streptavidin), hyaluronic acid, heparin, haptens, antibodies, and the like. Suitable dyes include, for example, fluorescent dyes such as fluorescein isothiocyanate (FITC), coumarin, Alexa Fluor, Cy3, Cy5, Oregon Green, Pacific Blue, Pacific Green, Pacific Orange, tetramethylrhodamine (TRITC), Texas Red, and the like.

Other features can include the following. The polyurea copolymer can be provided in solution in water, alcohol, an alcohol-water mixture, or a buffer. Thus, in some aspects, inventive concepts provide a composition comprising:
(a) a solvent selected from water, alcohol, an alcohol-water mixture, or a buffer; and
(b) a polyurea copolymer in solution, the polyurea copolymer comprising a reaction product of:
(i) a diamine composition comprising a polyethylene glycol diamine having a formula (I), (II), or a combination of diamines of formulae (I) and (II):

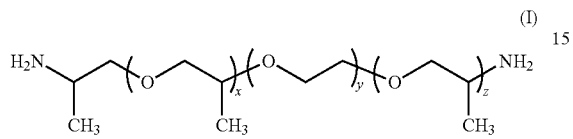
(I)

wherein y is an integer in the range of 2 to 40, and x+z is an integer in the range of 1 to 8; and

(II)

wherein n is an integer in the range of 1 to 500; and
(ii) a diisocyanate, wherein the diisocyanate is present in a molar ratio with total diamines in (i) in a range of 2:1 to 1:2, or a range of 1.3:1 to 1:1.3, or a range of 1.2:1 to 1:1.2, or in a range of 0.9:1 to 1.2:1. In some implementations, the diisocyanate is present in a 1:1 molar ratio, or in a 1.3:1 molar ratio, with total diamines in (i).

In some implementations, the diamine composition of (i) comprises a secondary amine version of the poly(ethylene glycol) diamine of formula (I), in which the amine end-groups are hindered secondary amine end groups represented by the terminal structure represented by formula (III) above. In these aspects, one reactive hydrogen on each end group provides for more selective reactivity. These embodiments can be useful for intermediate synthesis and intrinsically slower reactivity compared primary amines.

In some implementations, the diamine composition of (i) comprises a poly(propylene glycol) diamine having a formula (IV) or formula (V) as recited above.

Thus, in some aspects, the diamine composition can comprise any one of the diamines of Formulae (I) through (V), or a combination of any two or more of the diamines of Formulae (I) through (V). These diamine compositions are commercially available from Huntsman Corporation (The Woodlands, Tex., USA), under the JEFFAMINE® product lines, including JEFFAMINE® D, ED, EDR and SD series.

The polyurea copolymer solution can be put to a wide variety of uses, as will be apparent upon review of the present description.

In some aspects, the surface to which the coating composition is applied can be a surface that contacts biological fluids. The surface can be a surface of an implantable medical device, a medical device for temporary insertion into a patient's body, devices that contact biological fluids outside a patient's body (such as tubing or the like), or an in vitro diagnostic device. In other aspects, the surface to which the coating composition is applied can be a surface exposed to aqueous conditions for extended periods of time. The surface can be fabricated from a wide variety of materials, such as metal, polymer, ceramic, glass, fabric or biomaterial.

In a further aspect, a medical device is provided having a surface containing a passivating coating, the passivating coating comprising a polyurea copolymer that is a reaction product of:
(a) a diamine composition comprising a polyethylene glycol diamine having a formula (I), (II), or a mixture of (I) and (II):

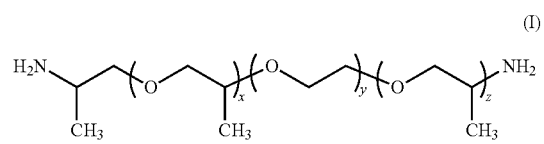
(I)

wherein y is an integer in the range of 2 to 40, and x+z is an integer in the range of 1 to 8; or

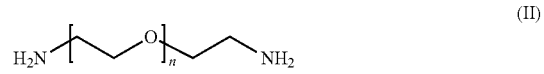
(II)

wherein n is an integer in the range of 1 to 500; and
(b) a diisocyanate, wherein the diisocyanate is present in a molar ratio with total diamines in (a) in a range of 2:1 to 1:2, or a range of 1.3:1 to 1:1.3, or a range of 1.2:1 to 1:1.2, or in a range of 0.9:1 to 1.2:1. In some implementations, the diisocyanate is present in a 1:1 molar ratio, or in a 1.3:1 molar ratio, with total diamines in (a).

The diamines of (a) can comprise any one of the diamines of Formulae (I) through (V), or a combination of any two or more of the diamines of Formulae (I) through (V).

Inventive polyurea copolymers, and coating compositions including these copolymers, can be provided to a wide variety of medical devices and diagnostics. In some embodiments, inventive polyurea copolymers can be applied to surfaces of microbeads, ophthalmic devices, neurological devices, and the like. In some aspects, the polyurea copolymer coating compositions can be uncrosslinked.

In still further aspects, methods for forming a passivating coating on a surface of a medical device comprise steps of:
(a) Providing a polyurea copolymer solution comprising a reaction product of (i) a diamine composition comprising a polyethylene glycol diamine having a formula (I), (II), or a mixture of (I) and (II):

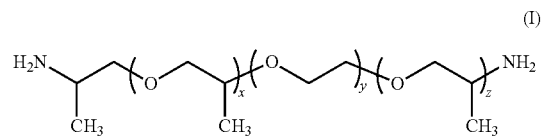
(I)

wherein y is an integer in the range of 2 to 40, and x+z is an integer in the range of 1 to 8; or

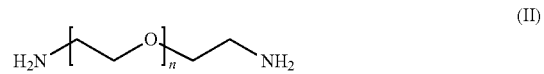
(II)

wherein n is an integer in the range of 1 to 500, and (ii) a diisocyanate, wherein the diisocyanate is present in a 1:1 molar ratio with total diamines in (i), the solution being provided in water, an alcohol, or an alcohol-water mixture;
   (b) Covering the surface of the medical device with the polyurea copolymer solution; and
   (c) Removing the polyurea copolymer solution from the surface.

The diamines of (a) can comprise any of the Formulae (I) through (IV), or a combination of any two or more of the diamines of Formulae (I) through (V).

The molar ratio of diisocyanate to total diamines can be in a range of 2:1 to 1:2, or a range of 1.3:1 to 1:1.3, or a range of 1.2:1 to 1:1.2, or in a range of 0.9:1 to 1.2:1. The diamine composition of (a) can further comprise a dipiperidyl alkane, wherein the diamine combination comprises 20 to 99.9 molar percent of the polyethylene glycol and 0.1 to 80 molar percent of the dipiperidyl alkane. Step (a) can comprise spraying the aqueous polyurea copolymer solution onto the surface or dipping the surface into the aqueous polyurea copolymer solution. Step (c) can comprise rinsing the surface with an aqueous solution. In some implementations, methods do not require a curing step.

It will be readily appreciated that inventive polyurea copolymer compositions can be used to provide a passivating coating on surfaces that are exposed to aqueous conditions for extended periods of time, such aquatic articles including, for example, water treatment system components (vessels, tanks, containers, filters, membranes, pipes, and the like), condenser coils, and/or marine vessels (such as boat or ship hulls, tanks, docks and the like), and marine vessel components (such as motors, anchors, rudders, and the like). Inventive polyurea copolymers can provide antifouling coating compositions on articles immersed or exposed to an aquatic environment. Such polyurea copolymer compositions, methods of coating, and coated articles, can apply the principles described herein.

The polyurea copolymers according to inventive concepts are easily synthesized under uncomplicated reaction conditions. In some implementations, the condensation reaction can take place at room temperature, or at a temperature in a range of about 20° C. to about 25° C. Optionally, the reaction can be mildly heated to temperatures below 100°; in some implementations, temperature need not be controlled during the reaction. In some aspects, the condensation reaction does not require an inert atmosphere and/or controlled pressure conditions. In some embodiments, inventive silicone polyurea copolymers can be formed by condensation polymerization under ambient room conditions (gas, temperature, pressure and/or humidity).

In accordance with inventive concepts, the reagents for polymerization, both diamines and diisocyanates, are soluble in alcohols or other common reaction solvents such as tetrahydrofuran (THF), ether, ethyl acetate, and other common organic solvents. The resulting reaction mixture solution has a low initial viscosity which facilitates mixing and enhances uniformity. During reaction, reagents can be added neat or as a solution. Each diamine or diisocyanate can be dissolved in the reaction solvent at the concentration used during polymerization with a viscosity less than 1000 cps, or less than 100 cps.

DETAILED DESCRIPTION

Inventive polyurea copolymers comprise polymerization products of the reaction of suitable di-functional amine monomer(s) with suitable di-functional isocyanate monomer(s). The di-functional monomers provide multiple urea linkages [—$R^aN$—(CO)—$NR^b$—], where (CO) defines a carbonyl group C=O, and each $R^a$ and $R^b$ is independently a hydrogen or an alkyl group. Diamine compositions used to form the polyurea copolymers include polyethylene glycol diamines, and, optionally, dipiperidyl alkanes. The urea linkages are located between polyethylene glycol segments of the copolymer. Thus, in context of the present disclosure, the term "polyurea" will be used to refer to these polymerization products. Without intending to be bound by a specific theory, it is the presence of multiple urea linkages, as well as polyethylene glycol within the copolymer backbone, that provide beneficial properties discussed herein. Further, synthesis of inventive polyurea copolymers is elegant and uncomplicated, providing ease of use.

For purposes of discussion herein, the polyurea copolymers are described as having a polymer backbone chain and two end-groups. In accordance with inventive concepts herein discussed, the polymer backbone has the following characteristics: consists of the longest series of covalently bonded atoms that together create the continuous chain of the copolymer; is the linear sequence of constitutional units to which all other chains, long or short or both, may be regarded as being pendant; and exists between two boundary constitutional units, each of which is referred to as an end-group. In some aspects, polyurea copolymers are linear (unbranched).

The reaction to produce the inventive polyurea copolymers involves mixing under reactive conditions the di-functional amine(s) and di-functional isocyanate(s) to produce a copolymer having passivating properties.

In some implementations, molecular weight of the polyurea copolymer is controlled. In some aspects, average molecular weight of the polyurea copolymer can be 100,000 or less, or 90,000 or less, or 80,000 or less, or 70,000 or less, or 60,000 or less, or 50,000 or less, or 40,000 or less, or 30,000 or less, or 20,000 or less, or an average molecular weight in a range of about 5,000 to about 100,000, or about 5,000 to about 90,000, or about 5,000 to about 80,000, or about 5,000 to about 70,000, or about 5,000 to about 60,000, or about 5,000 to about 50,000, or about 5,000 to about 40,000, or about 5,000 to about 30,000, or about 5,000 to about 20,000, or about 10,000 to about 15,000. Molecular weight can be controlled, for example, by controlling the size of monomers. Since monomers used are diamines and diisocyanates, monomers react via condensation to form the copolymer. The relatively low molecular weight of inventive polyurea copolymers can provide excellent solubility properties. Molecular weight can be adjusted to provide the desired solubility, considering starting monomers and the solvent used with the end polyurea copolymer product.

In some implementations, the polyurea polymerization reaction is in a molar ratio of diisocyanate to total diamines in a range of 1:2 to 2:1. The molecular weight of the resulting polymer can be controlled by the ratio of the two reactants. If one reactant is in excess, the other reactant will be the limiting reagent. As the ratio of excess increases, the molecular weight decreases because there is an insufficient molar amount of the limiting reagent to continue polymerization. For instance, if the feed ratio of the reaction is 1.3:1 diisocyanate to total diamine, the polymer will still contain alternating monomers from the diisocyanate and diamine linked by the urea, but both ends of the polymer will be isocyanate terminated and the length will be a statistical distribution determined theoretically by the ratio. The Carothers equation describes this state for a linear polymer with two monomers, where the limiting monomer is completely reacted as the number average of degree of polymerization $X_n$ as:

$X_n=(1+r)/(1-r)$ where $r$ is (molar ratio of monomer A)/(molar ratio of monomer B) where monomer B is in excess (e.g., for 1.3:1 $r=0.77$)

For 30% excess monomer, the degree of polymerization is 7.7 versus infinity for the perfectly 1:1 equimolar case. For 10% excess monomer, the degree of polymerization is 21. The degree of polymerization specifies the average number of monomer units in a polymer and can be converted to molecular weight by multiplying by the monomer weights. Therefore, the molecular weight can be controlled by altering the excess monomer ratio in the polymerization reaction. This effect for the inventive polyurea copolymers is demonstrated in the examples. Similarly, molecular weight is a factor in solubility, with molecular weight typically inversely proportional to solubility of a polymer in a given solvent. Altering the monomer ratio can therefore increase solubility of the resulting polyurea.

In some aspects, inventive polyurea copolymers contain relatively few repeating units of the di-functional amine monomer(s) and di-functional isocyanate monomer(s), given the reactivity of these starting materials. Thus, in some implementations, inventive polyurea copolymers can be considered oligomers, in that the structure of the copolymers essentially comprises a small plurality of units derived from molecules of lower relative molecular mass. For example, polyurea copolymers in accordance with inventive principles can include less than 40, or less than 30, or less than 20, or less than 10, or less than 9, or less than 8, or less than 7, or less than 6, or less than 5, or less than 4, or even 3 monomeric units. Such oligomeric species can be present within the polyurea copolymer reaction product, for example, in an amount up to about 25% of the total product. The presence of smaller molecular weight species may provide advantages, for example, for ease of manufacturing and/or solubility of the copolymer.

In a first aspect, a coating composition for a surface comprises a polyurea copolymer comprising a reaction product of:
(a) a diamine composition comprising a polyethylene glycol diamine having a formula (I), (II), or a combination of diamines of formulae (I) and (II):

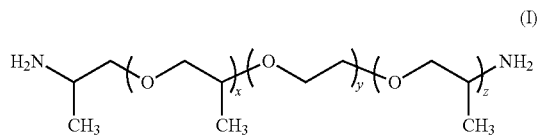

wherein y is an integer in the range of 2 to 40, and x+z is an integer in the range of 1 to 8; and

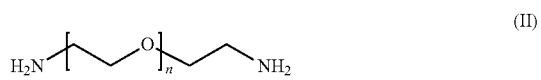

wherein n is an integer in the range of 1 to 500; and
(b) a diisocyanate, wherein the diisocyanate is present in a molar ratio with total diamines in (a) in a range of 2:1 to 1:2, or a range of 1.3:1 to 1:1.3, or a range of 1.2:1 to 1:1.2, or in a range of 0.9:1 to 1.2:1. In some implementations, the diisocyanate is present in a 1:1 molar ratio, or in a 1.3:1 molar ratio, with total diamines in (a). In some implementations, the diisocyanate is present in a 1:1 molar ratio with total diamines in (a). In some implementations, the diisocyanate is present in a 1.3:1 molar ratio with total diamines in (a).

The diamine composition of (a) can include the following variations. In some implementations, the diamine composition of (a) comprises a secondary amine version of the poly(ethylene glycol) diamine of formula (I), in which the amine end-groups are reacted with a ketone (e.g., acetone) and reduced to create hindered secondary amine end groups represented by the following terminal structure represented by formula (III):

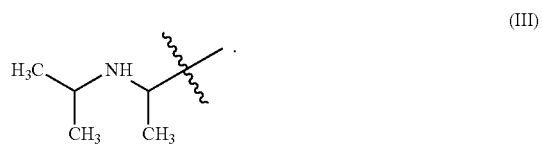 [SMILES: *C(C)NC(C)C]

In these aspects, one reactive hydrogen on each end group provides for more selective reactivity. These embodiments can be useful for intermediate synthesis and intrinsically slower reactivity compared primary amines.

In some implementations, the diamine composition of (a) comprises a poly(propylene glycol) diamine having a formula (IV):

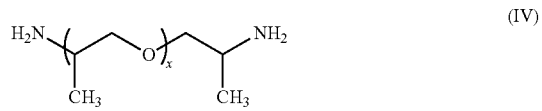

wherein x is an integer in the range of 2 to 70; or a poly(ethylene glycol) diamine having a formula (V):

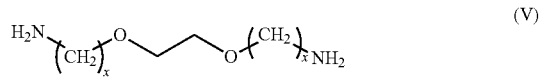

wherein x is 2 or 3.

Thus, in some aspects, the diamine composition of (a) can comprise any one of the diamines of Formulae (I) through (V), or a combination of any two or more of the diamines of Formulae (I) through (V). These diamine compositions are commercially available from Huntsman Corporation (The Woodlands, Tex., USA), under the JEFFAMINE® product lines, including JEFFAMINE® D, ED, EDR and SD series.

In some aspects, polyurea copolymers synthesized in accordance with inventive principles are soluble in water, alcohol (e.g., isopropanol), alcohol-water mixtures and buffer solutions. These polyurea copolymer compositions can preferentially bind to surfaces out of solution and provide a passivated surface. Not to be bound to theory, this may be due to a surfactant effect and/or to the urea linkages within the copolymer. Optionally, biomolecules can be included in the polyurea copolymer coatings described herein. Passivation provided by inventive polyurea copolymers can complement a biomolecule surface, as the polyurea copolymers can decrease denaturation of proteins during use of the surface for in vitro assays or in vivo. The polyurea copolymer can be provided in solution in water, alcohol, an alcohol-water mixture, or a buffer.

Thus, in some aspects, inventive concepts provide a composition comprising:
(a) a solvent selected from water, alcohol, an alcohol-water mixture, or a buffer; and
(b) a polyurea copolymer in solution, the polyurea copolymer comprising the reaction product of:
 (i) a diamine composition comprising a polyethylene glycol diamine having a formula (I), (II), or a combination of diamines of formulae (I) and (II):

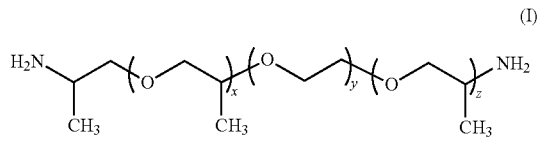

wherein y is an integer in the range of 2 to 40, and x+z is an integer in the range of 1 to 8; and

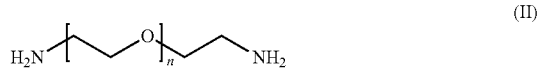

wherein n is an integer in the range of 1 to 500; and
 (ii) a diisocyanate, wherein the diisocyanate is present in a molar ratio with total diamines in (i) in a range of 2:1 to 1:2, or a range of 1.3:1 to 1:1.3, or a range of 1.2:1 to 1:1.2, or in a range of 0.9:1 to 1.2:1. In some implementations, the diisocyanate is present in a 1:1 molar ratio, or in a 1.3:1 molar ratio, with total diamines in (i).

Illustrative solvents include those listed as reaction solvents (THF, ethyl acetate, ether, dimethyl sulfoxide (DMSO), dimethylformamide (DMF), acetone, methyl ethyl ketone, chloroform, dichloromethane), as well as water, alcohol, water-alcohol mixtures, buffers, and other commonly used solvents. In some implementations, preferable solvents include alcohol, water, water-alcohol mixtures, and aqueous buffers.

As used herein, a "solution" refers to a homogeneous mixture composed of two or more substances, i.e., a solute dissolved in a solvent. Correspondingly, when a solute is dissolved in a solvent, it is referred to as "in solution." The term "aqueous solution" refers to any solution containing a solute dissolved in water. The term "buffer solution" is used in its common manner to include aqueous solutions consisting of a mixture of a weak acid and its conjugate base, or vice versa, wherein the solution resists change in pH when acid or alkali is added to it.

In some implementations, polyurea copolymers can be provided in solution, with a total solids content of 10% or lower, or 9% or lower, or 8% or lower, or 7% or lower, or 6% or lower, or 5% or lower, or 4% or lower, or 3% or lower, or 2% or lower, or 1% or lower. It will be appreciated the solids content of the solution can be selected depending upon final use of the polyurea copolymer solution.

Solubility refers to the property of the copolymer to dissolve in a solvent of choice. Slightly soluble means that about 100 to 1000 parts solvent, for example, are needed to dissolve 1 part solute, while "sparingly soluble" means that about 30 to 100 parts solvent, for example, are needed to dissolve 1 part solute. Soluble means that about 10 to 30 parts solvent, for example, are needed to dissolve 1 part solute. Freely soluble means that about 1 to 10 parts solvent, for example, are needed to dissolve 1 part solute. Very soluble (also referred to herein as "highly soluble") means that less than 1 part solvent is needed to dissolve 1 part solute.

Conversely, "insoluble" means that a copolymer is unable to dissolve in a solvent of choice, such as water, an alcohol, or an alcohol-water mixture.

Advantageously, polyurea copolymer compositions in accordance with inventive principles can provide durable coatings on surfaces. In some aspects, the adherence of a coating comprising inventive polyurea copolymer compositions is sufficient to withstand not only washing, but also contact of surfaces during use, for example, microsphere-microsphere contact upon magnetic separation.

Polyurea copolymers form coatings on many substrates. These coatings are generally films when more than a few monolayers are present (as in physisorption). The films themselves may be characterized either on a surface or as an isolated material by casting a polyurea coating solution, removing solvent by drying, and peeling up the resulting material. The material properties vary depending on the molecular weight of the polyurea and presence of crosslinking (e.g., when latent reactive groups are included).

In some aspects, inventive polyurea copolymers are generally lower molecular weight (Mw less than 100,000, or less than 50,000, or less than 20,000) and linear/unbranched. These polyurea copolymers are softer than many polyureas, with a Shore D Hardness Value of 30D or less, or 25D or less, or 20D or less, or 15D or less, or 10D or less.

In some implementations, inventive polyurea copolymers provide smooth, non-tacky coatings when applied to substrate surfaces. Smooth, non-tacky surfaces can be desirable for many industrial applications. In some aspects, inventive polyurea copolymers can exhibit a Young's modulus that is higher than known polyureas, for example greater than 1,000 psi (greater than 6,895,000 Pa), or greater than 2,000 psi, or greater than 3,000 psi. This modulus is greater than the Dahlquist criteria of 10,000 Pa used to define pressure sensitive adhesives.

Alternately, inventive polyurea copolymers can provide a coated surface that is mildly tacky to the touch. The degree of tackiness is insufficient to adhere an adherend with finger pressure or if it does, to be removed cleanly from the adherend. Because the polyurea copolymer coated surface is typically used under aqueous conditions (such as biological applications), a mild degree of tackiness does not impinge on performance. In many cases, the coating is too thin to be felt by finger touch. However, it is surprising that any degree of tackiness reduces protein and cellular adsorption given that tackiness is the mild adhesion of finger tip tissue, which is comprised of cells and proteins.

In additional aspects, inventive polyurea copolymers can be less brittle than higher molecular weight or branched polyureas. As a result, the tensile strength of inventive polyurea copolymers can be higher than many known polyureas, for example greater than 1,000 psi, or greater than 2,000 psi, or greater than 3,000 psi.

In some implementations, polyurea copolymer coatings can vary in thickness from a physisorbed monolayer of less than 10 nm to cast films that are greater than 1 mm in thickness. In some implementations, the coating thickness provided on a medical device or other article 10 microns or less, or 2 microns or less.

Additional advantages can be seen in the durability of coatings comprising inventive polyurea copolymer compositions. In some aspects, polyurea copolymer coated polystyrene plates are suitable for extended wash, incubation, and agitation steps. In addition, inventive polyurea copolymer coating compositions can bind to a large variety of substrate materials.

The stable binding of the polyurea copolymer to substrate is also surprising due to the lack of covalent bonding or heating step to induce polymer chain entanglement. Most PEG-based coatings require covalent bonding or they will be removed by rinsing, proteins or surfactant treatments. Optional components, such as latent reactive groups, can further enhance binding of the polyurea copolymer to substrate. However, it is understood such latent reactive groups are not required. Inventive coating processes are quite simple, the substrate to be coated is incubated in aqueous polyurea copolymer solution at room temperature, then rinsed with water. A curing step is not required; the coated substrate can be left to dry at room temperature in air. An inert atmosphere is not required. The polyurea copolymer can also be applied by spray, dip, or other coating method known to a person with skill in the art.

The resulting polyurea copolymer coated substrates demonstrate reduced adhesion of biomolecules including proteins, cells, tissue, bacteria, biofilm, and others. Examples show that microspheres coated with the polyurea copolymer have similar or improved passivation to that of bovine serum albumin (BSA), the gold standard of blockers for diagnostic assays such as ELISA, western blot, etc. In theory, this may be due to the polyethylene glycol (PEG) content of the polyureas; however, the magnitude of the passivation effect is much larger than typical PEG coatings. The urea linkage may also contribute to passivation due to hydrogen bonding or a chaotropic effect. The polyurea copolymer coating compared to a typical PEG-based coating is both better performing and more easily applied.

As used herein, "passivation" is the process of making a surface "passive," that is, a surface film or coating is created that results in a reduction of biological responses when exposed to biological fluids (for example, reduction of cellular attachment and proliferation, protein adsorption or reduction of cellular responses mediating inflammation). A passivating coating forms a surface having improved biological passivation as compared to the uncoated material, when exposed to conditions of use (for example, in a human body). Biological fluids (or "biofluids") can include intracellular fluid and extracellular fluid (intravascular, interstitial, lymphatic, transcellular), such as blood, saliva, urine, cerebrospinal fluid, blood plasma, ocular fluids (aqueous humour and vitreous humour), bile, lymph (endolymph and perilymph), exudates, gastric fluids (gastric acid, gastric juice), mucus, pericardial fluid, peritoneal fluid, pleural fluid, pus, rheum, sebum, serous fluid, semen, serum, amniotic fluid, and cerumen.

Similar concepts apply to surfaces that are maintained in an aqueous or humid environment for extended periods of time. Such surfaces can be rendered "passive" via the polyurea copolymer compositions described herein, such passivity being observed as reduced binding of unwanted materials (biological or chemical) to the surface. For example, inventive polyurea copolymers can be provided on a surface maintained in an aqueous environment to reduce formation of biofilms or other unwanted materials on the surface.

As used herein, the term "durability" refers to the wear resistance of a coating, or the ability of the inventive copolymer coatings to be maintained on a substrate surface when subjected to forces or conditions typically encountered during use (for example, normal force, shear force, and the like). A more durable coating is less easily removed from a substrate by abrasion. For applications involving long-term exposure to aqueous environments (such as water treatment vessels and/or lines), durability can refer to the ability of the coating to maintain a passivating surface on the application surface. Passivation properties can be measured using common techniques, based upon the application. Durability of a coating can be assessed by subjecting a substrate (such as a medical device) to conditions that simulate use conditions as is demonstrated in the Examples.

Inventive polyurea copolymers comprise a reaction product of: (a) a diamine composition comprising a polyethylene glycol diamine; and (b) a diisocyanate.

Suitable polyethylene glycol diamines can have a formula (I) or (II):

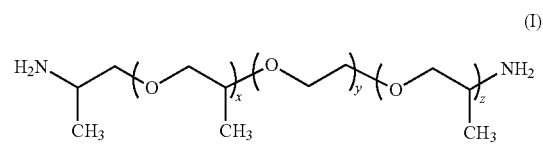

wherein y is an integer in the range of 2 to 40, and x+z is an integer in the range of 1 to 8; or

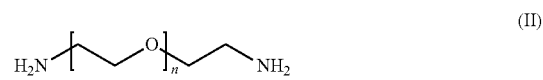

wherein n is an integer in the range of 1 to 500. The polyethylene glycol diamine can have a molecular weight of about 100 to about 35,000, or about 100 to about 25,000, or about 100 to about 10,000, or about 500 to about 25,000, or about 500 to about 10,000, or about 500 to about 5,000. In some implementations, the diamine composition includes a combination of polyethylene glycols of formula (I) and formula (II).

The diamine composition of (a) can comprise any one of the diamines of Formulae (I) through (V) described herein, or a combination of any two or more of the diamines of Formulae (I) through (V). These diamine compositions are commercially available from Huntsman Corporation (The Woodlands, Tex., USA), under the JEFFAMINE® product lines, including JEFFAMINE® D, ED, EDR and SD series.

Optionally, the diamine composition can further comprise a dipiperidyl alkane. In some aspects, the dipiperidyl alkane has a formula:

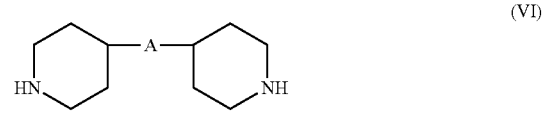

where A is a C0 to C8 bivalent alkyl radical. Illustrative dipiperidyl alkanes include dipiperidyl propane, dipiperidyl methane, dipiperidyl ethane, dipiperidyl butane, dipiperidyl pentane, dipiperidyl hexane, dipiperidyl heptane, and dipiperidyl octane, and bipiperidine.

In accordance with inventive concepts, when the dipiperidyl alkane is present, the diamine composition can comprise 20 to 99.9 molar percent of the polyethylene glycol and 0.1 to 80 molar percent of the dipiperidyl alkane.

As used herein, "alkyl" (by itself or as part of another substituent) refers to a saturated or unsaturated branched, straight-chain (linear), or cyclic monovalent hydrocarbon radical having the stated number of carbon atoms (for example, C1-C6 means one to six carbon atoms) that is derived by the removal of one hydrogen atom from a single carbon atom of a parent alkane, alkene or alkyne. Illustrative alkyl groups include, but are not limited to, methyl, ethyls (such as ethanyl, ethenyl, ethynyl), propyls, butyls, phenyls, and the like. It will be understood that "bivalent" alkyl radicals are derived from removal of two hydrogen atoms from a parent alkane, alkene or alkyne.

Surprisingly, it was found that several diamines produced copolymers that were completely insoluble in isopropanol and water. These diamines are thus less desirable for use in connection with inventive polyurea copolymers, since water and/or alcohol solubility is a significant advantage. As shown in the Examples, 1,3-diaminopropane, 1,3 diamino-2-propanol, cadaverine, lysine, and m-xylylenediamine produced copolymers that were completely insoluble. In some aspects, inventive polyurea copolymers are produced utilizing diamines compositions that do not comprise 1,3-diaminopropane, 1,3 diamino-2-propanol, cadaverine, lysine, and m-xylylenediamine. In some aspects, copolymers that do not include secondary alcohol functional groups can be advantageous. Thus, in some implementations, inventive copolymers do not include secondary alcohol functional groups.

Another surprising aspect of inventive polyurea copolymers is that silicone (i.e., polysiloxane and/or silane) is not required to provide a passivating surface. Silicone rubber surfaces are known for excellent biocompatibility and reduced non-specific protein and cell adhesion over other similar surfaces. The ability of inventive polyurea copolymers, which include blocks of polyethylene glycol but no siloxane (—Si—O—) and/or silane, to provide passivating surfaces that are comparable, or even improved over, polymers containing siloxane units, is thus surprising. Thus, in some aspects, inventive polyurea copolymers do not include siloxane and/or silane.

The diisocyanate used to prepare inventive polyurea copolymer compositions can have a formula:

OCN—B—NCO    (VII)

where B is a bivalent alkyl radical having 2 to 20 carbon atoms.

Illustrative monomeric diisocyanates include hexane diisocyanate, isophorone diisocyanate, naphthalene diisocyanate, toluene-2,4-diisocyanate, methylenediphenyldiisocyanate, p-phenyl enediisocyanate, meta-trimethylxylylenediisocyanate, methylene-bis(4-cyclohexylisocyanate), and hydrogenated methylenediphenyldiisocyanate. In some aspects, the diisocyanate is present in a molar ratio with total diamines in (a) in a range of 2:1 to 1:2, or a range of 1.3:1 to 1:1.3, or a range of 1.2:1 to 1:1.2, or in a range of 0.9:1 to 1.2:1. In some implementations, the diisocyanate is present in a 1:1 molar ratio, or in a 1.3:1 molar ratio, with total diamines in (a).

In some implementations, the relatively low molecular weight and bivalent character of monomeric units (diamines and diisocyanates) can provide polyurea copolymers having a relatively low molecular weight. This, in turn, can provide desirable solubility in aqueous solvent systems.

Methods of making polyurea copolymers are also provided. Inventive methods comprise polymerizing under reactive conditions:
(a) a diamine composition comprising a polyethylene glycol diamine having Formula (I) or (II) above, and, optionally, a dipiperidyl alkane; and
(b) a diisocyanate having a formula (VII) above.

In some implementations, the diamine composition of (a) can comprise any one of the diamines of Formulae (I) through (V) described herein, or a combination of any two or more of the diamines of Formulae (I) through (V). These diamine compositions are commercially available from Huntsman Corporation (The Woodlands, Tex., USA), under the JEFFAMINE® product lines, including JEFFAMINE® D, ED, EDR and SD series.

Optionally, the diamine composition can further comprise a dipiperidyl alkane. In some aspects, the dipiperidyl alkane has a formula:

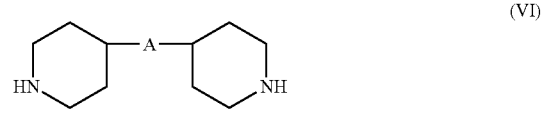

(VI)

where A is a C0 to C8 bivalent alkyl radical. Illustrative dipiperidyl alkanes include dipiperidyl propane, dipiperidyl methane, dipiperidyl ethane, dipiperidyl butane, dipiperidyl pentane, dipiperidyl hexane, dipiperidyl heptane, and dipiperidyl octane, and dipiperidine.

Advantageously, the reaction can be performed under relatively simple conditions, including mild solvents. Suitable reaction solvents are those which are unreactive with the diisocyanate(s) and which maintain the reactants and products in solution throughout the polymerization reaction. Useful reaction solvents include alcohol (such as isopropanol, methanol), tetrahydrofuran (THF), ether, ethyl acetate, and other common organic solvents. Typical reaction conditions are illustrated in the Examples. A condensation reaction can proceed at room temperature with stirring.

The resulting polyurea is a random copolymer with repeating diamine and diisocyanate units. Illustrative polyurea copolymers are provided in the Examples. In some aspects, the polyurea copolymer can comprise polyethylene glycol in amount in a range of 20 to 95, or 25 to 95 weight percent.

It has been found that resulting polyurea copolymers can include excess isocyanate at one or both polymer end groups. Over time, isocyanate can convert to amines, typically through reaction with water. Alternatively, the isocyanate group can intentionally be converted to an amine through standard reactions.

In some implementations, such amine groups can be utilized to provide desired components to the polyurea copolymers. Illustrative components include, but are not limited to, latent reactive groups, biomolecules and/or dyes.

Latent reactive groups can include photoreactive groups, thermally reactive groups and/or chemically reactive groups. These groups can be considered to be "latent" in that they remain stable and nonreactive during conditions of storage and can become chemically reactive when exposed to reaction conditions (such as an energy source, chemical composition, or other).

"Photoreactive groups" or "photo-activatable reactive chemical groups" are chemically inert compounds that become reactive when exposed to actinic energy. Typically, groups are chosen that can be activated using either ultraviolet or visible light. When exposed to an appropriate energy source, a photoreactive species undergoes a transformation from an inactive state (ground state) to a reactive intermediate capable of forming covalent bonds with appropriate materials. Useful photoreactive groups are described, for example, in U.S. Pat. No. 5,002,582 (Guire et al.) and U.S. Pat. No. 7,772,393 B2 (Guire et al.).

Illustrative photoreactive groups include, but are not limited to, aryl ketones, azides, diazos, diazirines, ketones, and quinones. The photoreactive groups generate active species such as free radicals including, for example, nitrenes, carbenes, and excited states of ketones upon absorption of electromagnetic energy.

In some implementations, the photoreactive group can be an aryl ketone, such as acetophenone, benzophenone, anthrone, and anthrone-like heterocycles (heterocyclic analogs of anthrone such as those having N, O, or S in the 10-position), or their substituted (for example, ring-substituted) derivatives. Examples of aryl ketones include heterocyclic derivatives of anthrone, including acridone, xanthone, and thioxanthone, and their ring substituted derivatives. Other suitable photoreactive groups include quinones such as, for example, anthraquinone.

Illustrative azides include arylazides such as phenyl azide and 4-fluoro-3-nitrophenyl azide; acyl azides (—CO—$N_3$) such as benzoyl azide and p-methylbenzoyl azide; azido formates (—O—CO—$N_3$) such as ethyl azidoformate and phenyl azidoformate; sulfonyl azides (—$SO_2$—$N_3$) such as benzenesulfonyl azide; and phosphoryl azides $(RO)_2PON_3$ such as diphenyl phosphoryl azide and diethyl phosphoryl azide.

Illustrative diazo compounds include diazoalkanes (—$CHN_2$) such as diazomethane and diphenyldiazomethane; diazoketones (—CO—$CHN_2$) such as diazoacetophenone and 1-trifluoromethyl-1-diazo-2-pentanone; diazoacetates (—O—CO—$CHN_2$) such as t-butyl diazoacetate and phenyl diazoacetate; and beta-keto-alpha-diazoacetates (—CO—$CN_2$—CO—O—) such as t-butyl alpha diazoacetoacetate. Diazo compounds are also thermally reactive groups.

Other photoreactive groups include diazirines (—$CHN_2$) such as 3-trifluoromethyl-3-phenyldiazirine, and ketenes (CH=C=O) such as ketene and diphenylketene.

Photoreactive groups can be non-ionic or ionic. Illustrative non-ionic photoreactive groups include the tetrakis (4-benzoylbenzyl ether) or the tetrakis (4-benzoylbenzyl ester) of pentaerythritol. Illustrative ionic photoreactive groups are discussed in US 2012/0258313 A1 (Wen et al.), U.S. Pat. No. 6,278,018 (Swan) and U.S. Pat. No. 5,714,360 (Swan et al).

In some implementations, latent reactive group(s) can comprise one or more thermally reactive groups. Thermal activation may be advantageous when exposure to UV light is not practical (for example for the inner lumen of a tubular medical article) or is undesirable (for example when coating materials contain UV light-sensitive components). Thermally reactive groups can also be advantageous in coatings exhibiting low transmission of UV light. Suitable external energy sources for these groups include heat sources.

Thermally reactive groups can include pairs of atoms having a heat sensitive (labile) bond between the atoms. Examples of such pairs of atoms include oxygen-oxygen (per-esters and peroxides), nitrogen-oxygen, and nitrogen-nitrogen. Examples of thermally reactive groups useful in present embodiments include 4,4' azobis(4-cyanopentanoic acid) and analogs of benzoyl peroxide. External energy sources to produce thermal energy can be used to activate a thermally reactive group.

In some embodiments, the latent reactive group can include one or more nitrenogenic groups. For example, a latent reactive group can comprise a perhalophenylazide (PHPA), such as perfluorophenylazide (PFPA). Perfluorophenylazides typically can be derived from 4-azido-2,3,5,6-tetrafluorobenzoic acid. A "nitrenogenic group" is a chemical moiety that becomes a nitrene group when exposed to a reaction-energy source. An azido group is an example of a nitrenogenic group. In turn, a "nitrene group" (also generally termed "nitrene" or "nitrene intermediate") is a particular form of nitrogen group regarded as the nitrogen analog of carbenes. Like carbenes, nitrenes are generally regarded as intermediates that are highly reactive and may not be isolatable under ordinary conditions. Important nitrene reactions include, but are not limited to, addition or insertion in C—H, N—H, O—H, and C—C bonds (single and double).

In some implementations, the latent reactive groups can comprise chemical reactive groups. Suitable chemical reactive groups can be referred to as redox initiators, redox catalysis agents, or redox activation agents. In general, combinations of organic and inorganic oxidizers, and organic and inorganic reducing agents are used to generate radicals for polymerization. A description of redox initiation can be found in *Principles of Polymerization,* $2^{nd}$ Edition, Odian G., John Wiley and Sons, pages 201-204 (1981), that part of which is herein incorporated by reference. In some implementations, the chemical reactive group can comprise a catechol-based group, such as catecholamine (that is, dopamine, or 4-(2-aminoethyl)benzene-1,2-diol), and such groups can be activated with oxidizing agents.

In some implementations, polyurea copolymers can include one or more biomolecules or dyes. In accordance with inventive principles, biomolecules can be selected to provide additional features to the copolymer, such as binding sites for additional components (thus creating customizable copolymers), antimicrobial properties, passivating properties, activation of enzymes, conjugation of antibodies, and the like.

Illustrative biomolecules include saccharides (mono- and polysaccharides), proteins, nucleic acids, and the like. Illustrative saccharides include hyaluronic acid, heparin, glycosaminoglycans, chitosan, glucosamines, and the like. Illustrative proteins include avidin (including streptavidin); antibodies; albumin, globulin, fibrinogen, and other blood proteins; enzymes; collagen, fibronectin, elastin, laminin, and other extracellular matrix proteins.

When included, dyes can be selected to provide suitable visualization tools for the desired application. Illustrative dyes include fluorescent dyes such as green fluorescent protein (GFP), fluorescein isothiocyanate (FITC), coumarin, Alexa Fluor, Cy3, Cy5, Oregon Green, Pacific Blue, Pacific Green, Pacific Orange, tetramethylrhodamine (TRITC), Texas Red, and the like.

In accordance with inventive concepts, polyurea copolymers can be prepared to include latent reactive groups, biomolecules, dyes, or a combination of any two or more of these, in a number of ways. In some implementations, these additional components are not provided during polymerization of the polyurea copolymer; rather, they are introduced to the formed polyurea copolymer after it has been synthesized. This can be beneficial when it is desirable to synthesize a linear (nonbranched) polyurea copolymer. When additional components are provided to the polyurea copolymer after condensation polymerization is completed, these additional components do not impact polymerization by introducing branching or crosslinking of the polyurea copolymer during polymerization. In this manner, addition of components such as latent reactive groups, biomolecules and/or dyes is orthogonal to polymerization of the polyurea copolymer.

In some implementations, isocyanate and/or amine groups present in the copolymer are used to couple latent reactive groups, biomolecules and/or dyes to the polyurea copolymer. Typically, polyurea copolymers prepared in accordance with methods described herein include an excess of isocyanate end groups. These electrophilic groups are reactive toward a variety of nucleophiles, including alcohols, amines and even water. Thus, when stored over time in a solvent such as water or alcohol, these isocyanate groups can form amine groups. These isocyanate and/or amine groups can easily be utilized to couple latent reactive groups, biomolecules and/or dyes to inventive polyurea copolymers. Such coupling can take place in solution, while the polyurea copolymer is synthesized, after the polyurea copolymer is synthesized but before application to a surface of interest, and/or after a polyurea copolymer has been applied to a substrate surface.

When di-amine latent reactive groups are combined with inventive diamine compositions comprising a polyethylene glycol diamine and a diisocyanate, in reaction solvent (e.g., an alcohol), resulting polyurea copolymers can include the latent reactive groups or biomolecules incorporated within the copolymer backbone, or pendant to the copolymer backbone (i.e., at the end-groups). It is understood that mono-amine compounds would provide end-group coupling, while di-amine compounds could be incorporated into the copolymer backbone and/or at copolymer chain end-groups.

In some implementations, naturally occurring amine end groups of the polyurea copolymer can be coupled with latent reactive groups and/or biomolecules through use of synthetic chemical groups. Numerous synthetic chemical groups exist that will form chemical bonds with primary amines. These include, for example, carboxylate, thiol, maleimide, aldehydes, NHS esters, toluenesulfonyl (tosyl), isothiocyanates, isocyanates, acyl azides, sulfonyl chlorides, glyoxals, epoxides, oxiranes, carbonates, aryl halides, imidoesters, carbodiimides, anhydrides, fluorophenyl esters, alkyne, azide, phosphine, phosphite, and the like. Many of these conjugate to amines by either acylation or alkylation. Standard coupling chemistry can be used to transform naturally occurring amine groups at the polyurea copolymer end groups.

In some implementations, amine end groups of the polyurea copolymer can be transformed into other biomolecule-reactive groups such as NHS, epoxide, carboxylate, maleimide, or the like, so that a reactive coating can be applied to a surface. The reactive surface can then later be functionalized with a biomolecule selected by an end user through the biomolecule-reactive group chemistry.

In accordance with inventive principles, latent reactive groups (such as photoreactive groups) can be chosen that do not adversely affect solubility of the polyurea copolymers. Such latent reactive groups can themselves be soluble in water, alcohol, alcohol-water, or buffer solutions. Alternatively, less soluble latent reactive groups can be added in molar amounts that do not affect the overall solubility of the polyurea.

Some illustrative reaction conditions are provided in the Examples.

Novel polyurea copolymers produced in accordance with inventive principles can be used as coating compositions for a wide variety of surfaces. In some aspects, such coating compositions can be particularly useful when utilized in connection with surfaces that contact biological fluids. The surface can be a surface of an implantable medical device, a medical device for temporary insertion into a patient's body, devices that contact biological fluids outside a patient's body (such as tubing or the like), or an in vitro diagnostic device. Inventive polyurea copolymer compositions can also be applied to substrates outside the implantable medical device field, as will be apparent from the variety of materials that can be coated with the inventive polyurea copolymers. Illustrative classes of substrates outside the medical device field include water treatment system components and aquatic apparatus and systems (such as ships, boats, tanks, pipes, docks, and the like).

The particular form of the substrate is not critical. In accordance with inventive aspects, the substrates can be provided in a number of different formats. Illustrative substrates include, for example, solid tangible surfaces and particles.

Suitable materials for fabrication of solid tangible surfaces include materials commonly used to fabricate implantable medical devices. The solid tangible surface is optionally intended to function in contact with tissue and/or fluids of the body. Examples of suitable support materials include those materials commonly used to fabricate implantable medical devices such as metals, minerals or ceramics, fabric, carbon-based materials (e.g., biomaterial), and polymers.

Suitable metals include, for example, aluminum, chromium, cobalt, iron, tantalum, titanium, and alloys thereof, as well as nitinol and other nickel-titanium alloys, and stainless steels. Examples of suitable minerals or ceramics include alumina, hydroxyapatite, quartz, sapphire, silica and glasses. Illustrative carbon-based materials include pyrolytic carbon, as well as carbon materials obtained by thermal degradation (thermolysis, pyrolysis) or organic compounds, as well as materials obtained by physical vapor deposition (PVD) techniques.

In some aspects, the polyurea copolymers can be useful in connection with substrates fabricated of a synthetic or natural polymer. For example, the substrate can be fabricated from synthetic polymer such as Parylene™ (tradename for a variety of chemical vapor deposited poly(p-xylylene) polymers), polyamides (such as polyether block amides such as PEBAX™) polyesters, polyethylenes, polyethylene terephthalates (PET), poly(meth)acrylates, polyacetates, polyvinylacetates, sulfonic acid-substituted polymers, polyacrylamide polyethylene glycols, polyethyleneimines, polylactic acids, polyglycolic acids, polylactide-co-glycolides, polyvinyl alcohols, polyvinyl pyrrolidones, quaternary amine-substituted polymers, conductive polymers (for example, polyvinylpyridine, polyacetylenes, polypyrroles), poly-(p-pheyleneterephthalamides), polyphosphazenes, polypropylenes, polyetetrafluoroethylenes, polysiloxanes, inorganic synthetic elastomers, organic polymers, or copolymers thereof or combinations of any of these. In other embodiments, the substrate can be formed from natural polymers such as polysaccharides, proteins, nucleic acids or organic polymers.

In some aspects, a suitable substrate can be fabricated of a polymeric material. Exemplary polymers include silicones, polyolefins, vinyl polymers, polystyrenes, polyacrylates (including polymethacrylate), poly(methyl)methacrylates, polyacrylonitriles, poly(vinylacetates), poly (vinyl alcohols), chlorine-containing polymers such as poly(vinyl) chloride, polyoxymethylenes, polycarbonates, polyamides, polyimides, polyurethanes, phenolics, amino-epoxy resins, polyesters, cellulose-based plastics, and rubber-like plastics, providing surfaces that can be modified as described herein. See generally, "Plastics", pp. 462-464, in Concise Encyclopedia of Polymer Science and Engineering, Kroschwitz, ed., John Wiley and Sons, 1990. Illustrative polyolefins include polyethylene, such as high density polyethylene (HDPE), polytetrafluoroethylene, and the like, as well as polypropylene and the like.

In some implementations, polyurea copolymers are provided as coatings on implantable medical devices. Illustrative implantable medical devices include, but are not limited to, vascular devices such as guidewires, stents, stent grafts, covered stents, catheters (single use and long-term), valves, distal protection devices, aneurysm occlusion devices, septal defect closures; cardiac devices such as artificial hearts and heart assist devices such as defibrillators, pacemakers and pacing leads; orthopedic devices such as joint implants and fracture repair devices; dental devices such as dental implants and repair devices; ocular devices and glaucoma drain shunts; urological devices such as penile, sphincter, urethral, bladder and renal devices; neurological devices such as neurostimulators, drainage catheters, shunts, fixation devices, coils (e.g., embolization), electrodes, myeloscopes, guidewires, stents, grafts, probes, meshes, and matrices; synthetic prostheses such as breast prostheses and artificial organs; surgical closures; laparoscopic fixation devices; endosurgical components; tracheal, esophageal or bronchial tubes; ear tube components; fixation devices (plates, screws, tacks, pins, nails); shunts; dialysis components; filters; ports; sensors; scaffolds; patches; and the like. In some implementations, the medical article is a catheter, such as a silicone catheter.

Non-implanted medical articles can be provided with inventive coatings as well, including such articles as transdermal drug delivery devices (such as patches, bandages, dressings, and the like); dialysis devices and associated tubing, catheters, membranes and grafts; autotransfusion devices; vascular and surgical devices including a wide variety of catheters (atherectomy, angiographic, clot extraction, angioplasty, electrophysiology, and the like), intraaortic balloon pumps, intracardiac suction devices, blood pumps, blood oxygenator devices (including tubing and membranes), blood filters, blood temperature monitors, hemoperfusion units, plasmapheresis units, transition sheaths, dialators, intrauterine pressure devices, breathing circuit connectors, stylets (vascular and non-vascular), guidewires (coronary, peripheral, and the like); dialators (e.g., urinary, etc.); surgical instruments (e.g., scalpels and the like); endoscopic devices (such as endoscopic surgical tissue extractors, esophageal stethoscopes); hearing aids; and general medical and medically related devices including blood storage bags, umbilical tape, membranes, wound dressings (including bandages), wound management devices, needles, percutaneous closure devices, transducer protectors, uterine bleeding patches, clamps, cannulae; as well as diagnostic slides (such as oligonucleotide arrays, microarrays, protein chips and fluorescence in situ hybridization (FISH) slides); chromatographic support materials; cell culture devices; biosensors; microfluidic devices; and the like.

Non-implanted medical devices include, but are not limited to, diagnostic slides such as gene chips, DNA chip arrays, microarrays, protein chips, and fluorescence in situ hybridization (FISH) slides; arrays including cDNA arrays, and oligonucleotide arrays; chromatographic support materials, cell culture devices, biosensors, and the like.

Generally speaking, in vitro diagnostics (IVD) are considered medical devices. In accordance with inventive concepts, medical diagnostics include articles used in vitro for the examination of specimens such as blood, urine or tissue with the goal of obtaining a diagnosis from assays in a controlled environment outside a living organism. Medical diagnostics can include laboratory consumables (plates, tubes, trays, capillaries, containers, and the like), cell culture ware, slides, assays, microarrays, sensors, and the like.

In some implementations, inventive polyurea copolymers can be used to passivate the surface of microparticles, such as magnetic microparticles. Illustrative particles include micro- and nanoparticles including but not limited to magnetic particles, polystyrene particles, metallic particles. Additional devices include microwell and larger plates; slides; membranes; tubing; gels; petri dishes; cell cultureware including but not limited to flasks, plates, tubes, and vials; bioreactors; aquatic or marine vessels and structures and other surfaces subject to biofouling; catheters; guidewires; introducers; sensor surfaces; and other medical device surfaces.

In further aspects, inventive concepts provide an article, such as a medical device or aquatic article, the article having a surface containing a passivating coating, the passivating coating comprising a polyurea copolymer comprising a reaction product of: (a) a diamine composition comprising a polyethylene glycol diamine; and (b) a diisocyanate. Components (a) and (b) are as described herein.

Inventive concepts also provide methods for forming a passivating coating on a surface of a medical device comprising steps of:

(a) Providing a polyurea copolymer solution comprising a reaction product of (i) a diamine composition comprising a polyethylene glycol diamine; and (ii) a diisocyanate, the reaction product being provided in water, an alcohol, or an alcohol-water mixture;

(b) Covering the surface of the medical device with the polyurea copolymer solution; and (c) Removing the polyurea copolymer solution from the surface.

The diamine composition of (i) and diisocyanate of (ii) are as described elsewhere herein. The polyurea copolymer solution can be provided onto the surface by any suitable method, including spray coating, immersion, spreading the solution onto the surface, and the like. The polyurea copolymer solution can be removed from the surface by any suitable method, such as rinsing with a solution that is the same as the solvent for the polyurea copolymer solution (e.g., water, alcohol, or an alcohol-water mixture). Advantageously, some embodiments of the inventive methods do not include a curing step, such as by UV illumination, heating to a desired temperature, or the like.

In some implementations, inventive polyurea copolymers adhere to a surface through adsorption, more specifically, physisorption. As contemplated herein, physisorption involves adsorption in which the forces involved are intermolecular forces (van der Waals forces), and which do not involve a significant change in the electronic orbital patters of the species involved. In the case of physisorption, the adsorbed species (coated polyurea copolymers) are chemically identical with those in the fluid phase, so that the chemical nature of the fluid is not altered by adsorption and subsequent desorption. Equilibrium is established between the adsorbate and the fluid phase. In some aspects, physisorption can take place in water, alcohol, alcohol-water mixtures or buffers. Association of polyurea copolymers via physisorption can have significant advantages, since the polyurea copolymers associate with a surface without drying. Thus, the ability to coat polyurea copolymers onto a surface via inventive concepts can provide more uniform coatings through this occurrence of physisorption. In some implementations, inventive polyurea copolymers can provide multiple coating layers on a surface. This is in contrast to chemisorption, where the adsorbed molecules are linked to the surface by valence bonds and thus typically occupy certain adsorption sites on the surface, resulting in only one layer of chemisorbed molecules (monolayer adsorption).

Surfaces can also be coated by dipcoating, casting, or spray coating. In these cases, the polyurea copolymer is formed prior to coating and applied as a single solution, in contrast to a two part pre-polymer spray polyurea application that undergoes chemical reaction upon combination in the spray. In accordance with inventive concepts, surfaces can be coated by simply dipping into the polyurea copolymer solution and air drying to remove the solvent. Illustrative solvents include alcohols, water, alcohol-water mixtures, and buffer solutions.

In some aspects, coating thickness and uniformity can be controlled by extraction rate and dwell time, and other techniques known to persons skilled in the art. The polyurea copolymer coating can be applied as one coated layer, or as several layers. The polyurea copolymer coating can be applied as a topcoat over a primer layer if desired, or as a primer layer to increase adhesion for a subsequent topcoat of either further polyureas or alternate non-polyurea coatings meant to improve the surface properties of the substrate.

In some implementations, the polyurea copolymer may be functionalized with reactive groups to allow further chemical bonding of biomolecules after coating; however, this chemical reaction is distinct from further polymerization of diisocyanate and diamine. Advantageously, the polyurea copolymer coatings do not require crosslinking to remain on the surface; however, crosslinking by latent reactive groups, such as photoactivable groups, can be used to increase durability to use conditions. For example, polyurea copolymers containing 4,4'-diaminobenzophenone, can be photoactivated to form covalent bonds between the polyurea copolymer and the substrate and/or between the polyurea copolymers and/or between the polyurea copolymer and other molecules that are desired on the surface. These new covalent bonds can connect a polyurea copolymer coating to a substrate, increase durability of a polyurea copolymer coating, or immobilize additional coating layers and/or coating components such as other non-polyurea polymers. Further illustration is provided in the examples. The latent reactive groups used in this manner are distinct from and do not include the diisocyanate/diamine chemistry used to crosslink other polyurea coatings.

The embodiments of the present invention described herein are not intended to be exhaustive or to limit the invention to the precise forms disclosed. Rather, the embodiments are chosen and described so that others skilled in the art can appreciate and understand the principles and practices of the present invention. This application is intended to cover adaptations or variations of the present subject matter.

All publications and patents mentioned herein are hereby incorporated by reference to the same extent as if each individual publication or patent application was specifically and individually indicated by reference. The publications and patents disclosed herein are provided solely for their disclosure. Nothing herein is to be construed as an admission that the inventors are not entitled to antedate any publication and/or patent. Including any publication and/or patent cited herein.

In the specification and in the claims, the terms "including" and "comprising" are open-ended terms and should be interpreted to mean "including, but not limited to . . . ". These terms are broader than, and therefore encompass, the more restrictive terms "consisting essentially of" and "consisting of."

As used herein and in the appended claims, the singular forms "a," "an," and "the" include plural reference unless the context clearly dictates otherwise. As such, the terms "a" (or "an"), "one or more" and "at least one" can be used interchangeably herein.

Examples 1-4. Polyurea Copolymer Synthesis

Example 1

A polyurea copolymer was synthesized by combining 2.0099 grams of Jeffamine™ ED1900 (1 mmole, Sigma Aldrich, Milwaukee, Wis.) and 0.2116 grams dipiperidyl propane (1 mmole, Sigma Aldrich, Milwaukee, Wis.) in 15 ml of isopropanol. To this, 0.415 ml of hexane diisocyanate (2.6 mmoles, Sigma Aldrich, Milwaukee, Wis.) was added. The reaction mixture was stirred vigorously at room temperature for 1 hour, then used without further purification.

Example 2

A polyurea copolymer was synthesized by combining 0.580 grams of Jeffamine™ ED600 (1 mmole, Sigma Aldrich, Milwaukee, Wis.) and 0.2128 grams dipiperidyl propane (1 mmole, Sigma Aldrich, Milwaukee, Wis.) in 5 ml of isopropanol. To this, 0.415 ml of hexane diisocyanate (2.6 mmoles, Sigma Aldrich, Milwaukee, Wis.) was added. The reaction mixture was stirred vigorously at room temperature for 1 hour, then used without further purification.

Example 3

A polyurea copolymer was synthesized by combining 0.41 grams of Jeffamine™ ED600 (0.7 mmole, Sigma Aldrich, Milwaukee, Wis.) and 0.2703 grams dipiperidyl propane (1.3 mmole, Sigma Aldrich, Milwaukee, Wis.) in 15 ml of isopropanol. To this, 0.415 ml of hexane diisocyanate (2.6 mmoles, Sigma Aldrich, Milwaukee, Wis.) was added. The reaction mixture was stirred vigorously at room temperature for 1 hour, then used without further purification.

Example 4

A polyurea copolymer was synthesized by combining 0.2432 grams of Jeffamine™ ED600 (0.4 mmole, Sigma Aldrich, Milwaukee, Wis.) and 0.3415 grams dipiperidyl propane (1.6 mmole, Sigma Aldrich, Milwaukee, Wis.) in 15 ml of isopropanol. To this, 0.415 ml of hexane diisocyanate (2.6 mmoles, Sigma Aldrich, Milwaukee, Wis.) was added. The reaction mixture was stirred vigorously at room temperature for 1 hour, then used without further purification. The resulting copolymer was soluble in isopropanol.

Examples 5-12. Polyurea Copolymer Synthesis, Insoluble in Isopropanol

Example 5

A polyurea copolymer was synthesized by combining 0.1313 grams of Jeffamine™ ED600 (0.2 mmole, Sigma Aldrich, Milwaukee, Wis.) and 0.3826 grams dipiperidyl propane (1.8 mmole, Sigma Aldrich, Milwaukee, Wis.) in 15 ml of isopropanol. To this, 0.415 ml of hexane diisocyanate (2.6 mmoles, Sigma Aldrich, Milwaukee, Wis.) was added. The reaction mixture precipitated vigorously, the resulting white copolymer was insoluble in isopropanol.

Example 6

A polyurea copolymer was synthesized by combining 0.13 ml of m-xylylene diamine (1.0 mmole, Sigma Aldrich, Milwaukee, Wis.) and 0.2107 grams dipiperidyl propane (1.0 mmole, Sigma Aldrich, Milwaukee, Wis.) in 15 ml of isopropanol. To this, 0.415 ml of hexane diisocyanate (2.6 mmoles, Sigma Aldrich, Milwaukee, Wis.) was added. The reaction mixture precipitated vigorously, the resulting white copolymer was insoluble in isopropanol.

Example 7

A polyurea copolymer was synthesized by combining 0.13 ml of m-xylylene diamine (1.0 mmole, Sigma Aldrich, Milwaukee, Wis.) and 0.6026 grams Jeffamine™ ED600 (1.0 mmole, Sigma Aldrich, Milwaukee, Wis.) in 15 ml of isopropanol. To this, 0.415 ml of hexane diisocyanate (2.6 mmoles, Sigma Aldrich, Milwaukee, Wis.) was added. The reaction mixture precipitated vigorously, the resulting white copolymer was insoluble in isopropanol.

Example 8

A polyurea copolymer was synthesized by combining 0.12 grams of cadaverine (1.0 mmole, Sigma Aldrich, Milwaukee, Wis.) and 0.6020 grams Jeffamine™ ED600 (1.0 mmole, Sigma Aldrich, Milwaukee, Wis.) in 15 ml of isopropanol. To this, 0.415 ml of hexane diisocyanate (2.6 mmoles, Sigma Aldrich, Milwaukee, Wis.) was added. The reaction mixture precipitated vigorously, the resulting white copolymer was insoluble in isopropanol.

Example 9

A polyurea copolymer was synthesized by combining 0.0764 grams 1,3-diamino-2-hydroxy-propane (0.8 mmole, Sigma Aldrich, Milwaukee, Wis.) and 0.2186 grams dipiperidyl propane (1.0 mmole, Sigma Aldrich, Milwaukee, Wis.) in 15 ml of isopropanol. To this, 0.415 ml of hexane diisocyanate (2.6 mmoles, Sigma Aldrich, Milwaukee, Wis.) was added. The reaction mixture precipitated vigorously, the resulting white copolymer was insoluble in isopropanol.

Example 10

A polyurea copolymer was synthesized by combining 0.07 ml of 1,3-diaminopropane (1.0 mmole, Sigma Aldrich, Milwaukee, Wis.) and 0.2108 grams dipiperidyl propane (1.0 mmole, Sigma Aldrich, Milwaukee, Wis.) in 15 ml of isopropanol. To this, 0.415 ml of hexane diisocyanate (2.6 mmoles, Sigma Aldrich, Milwaukee, Wis.) was added. The reaction mixture precipitated vigorously, the resulting white copolymer was insoluble in isopropanol.

Example 11

A polyurea copolymer was synthesized by combining 0.07 ml of 1,3-diaminopropane (1.0 mmole, Sigma Aldrich, Milwaukee, Wis.) and 0.6153 grams Jeffamine™ ED600 (1.0 mmole, Sigma Aldrich, Milwaukee, Wis.) in 15 ml of isopropanol. To this, 0.415 ml of hexane diisocyanate (2.6 mmoles, Sigma Aldrich, Milwaukee, Wis.) was added. The reaction mixture precipitated vigorously, the resulting white copolymer was insoluble in isopropanol.

Example 12

A polyurea copolymer was synthesized by combining 0.0954 grams 1,3-diamino-2-hydroxy-propane (1.0 mmole, Sigma Aldrich, Milwaukee, Wis.) and 0.6147 grams Jeffamine™ ED600 (1.0 mmole, Sigma Aldrich, Milwaukee, Wis.) in 15 ml of isopropanol. To this, 0.415 ml of hexane diisocyanate (2.6 mmoles, Sigma Aldrich, Milwaukee, Wis.) was added. The reaction mixture precipitated vigorously, the resulting white copolymer was insoluble in isopropanol.

Example 13. Polyurea Copolymer Synthesis, Isophorone Diisocyanate

A polyurea copolymer was synthesized by combining 2.0363 grams of Jeffamine™ ED1900 (1 mmole, Sigma Aldrich, Milwaukee, Wis.) and 0.2128 grams dipiperidyl propane (1 mmole, Sigma Aldrich, Milwaukee, Wis.) in 15 ml of isopropanol. To this, 0.50 ml of isophorone diisocyanate (2.4 mmoles, Sigma Aldrich, Milwaukee, Wis.) was added with stirring for 15 minutes at room temperature. The resulting product was soluble in isopropanol. The reaction mixture was stirred vigorously at room temperature for 1 hour, then used without further purification.

Example 14. Passivation Via Direct ELISA Assay

To 12 wells each in a 96-well plate, 100 uL of 1× phosphate buffered saline (PBS, Gibco/ThermoFisher, Grand Island, N.Y.), 100 uL of 10 ug/ml goat IgG (Lampire Biological, Pipersville, Pa.) in PBS, and 100 uL of 10 ug/ml Rabbit IgG (Lampire Biological, Pipersville, Pa.) in PBS was added. The plate with the filled wells was shaken orbitally at room temperature for one hour in the dark to adsorb the IgG to the well surfaces. After one hour, the wells were all washed twice with PBS. To 4 of each type of coated well (none, goat IgG, or Rabbit IgG), 125 uL of PBS was added. To 4 of each type of coated well (none, goat IgG, or Rabbit IgG), 125 uL of 1% BSA (bovine serum albumin, Sigma Aldrich, St. Louis, Mo.) in PBS was added. To 4 of each type of coated well (none, goat IgG, or Rabbit IgG), 125 uL of a solution of Example 1, diluted to 1:100 in PBS, was added. The 96 well plate was orbitally shaken at room temperature in the dark for one hour.

After one hour, all wells were washed twice with PBS, then 75 uL of a 1:100,000 dilution of mouse anti-rabbit IgG-horseradish peroxidase (Sigma Aldrich, St. Louis, Mo.) in PBS was added to each well. The 96 well plate was then orbitally shaken at room temperature in the dark for one hour. After one hour, the wells were all rinsed twice with PBS, the plate was inverted to remove any remaining solution, then 50 ul/well of TMB developing solution (KPL/Seracare, Milford, Mass.) was added and the plate was orbitally shaken at room temperature in the dark for 10 minutes. After 10 minutes, 50 ul/well of 0.5N sulfuric acid was added to stop the reaction and the optical density of the solutions in each well was measured at 450 nm. Results of the experiment in triplicate were averaged and normalized with the no primary antibody/no blocker condition as 1.0. The blocker from Example 1 performed statistically equivalent to BSA.

TABLE 1

| 1° Ab/Ag | Blocker | Ave A450 | St. Dev. |
|---|---|---|---|
| none | None | 1.000 | 0.000 |
| GtIgG | None | 0.242 | 0.030 |
| RbIgG | None | 0.920 | 0.108 |
| none | BSA | 0.017 | 0.004 |
| GtIgG | BSA | 0.035 | 0.059 |
| RbIgG | BSA | 0.825 | 0.122 |
| none | Example 1 | 0.038 | 0.004 |
| GtIgG | Example 1 | 0.024 | 0.009 |
| RbIgG | Example 1 | 0.828 | 0.101 |

Example 15. Polyurea Copolymer Synthesis

A polyurea copolymer was synthesized by combining 4.0023 grams of Jeffamine™ ED1900 (2.0 mmole, Sigma Aldrich, Milwaukee, Wis.) and 0.415 ml of hexane diisocyanate (2.6 mmoles, Sigma Aldrich, Milwaukee, Wis.) in 15 ml of isopropanol. The reaction mixture was stirred vigorously at room temperature for 1 hour, then used without further purification. The resulting product was soluble in isopropanol.

Example 16. Passivation Against Mammalian Cell Attachment

To determine the effect of the polyurea copolymer coating on mammalian cells, each polyurea product, synthesized as described in Examples 13, 31-d, 31-e, and 31-f, was diluted to 1 g/L in isopropanol and applied to 96-well tissue culture polystyrene (TCPS) plates. Aliquots of each formula were applied to 8 wells for evaluation. 25-30 µl of polyurea copolymer coating solution was added to each well, the solution dwelled in the well for 30 seconds, then the coating solution was removed by aspiration. The plates were then air dried overnight in a class II laminar flow biosafety cabinet, to remove residual isopropanol. The next day, the coated plates were rinsed 3×10 minutes with 100-200 µl cell culture grade water per well, prior to cell seeding. Control wells were generated by substitution of isopropanol for coating solution.

Human dermal fibroblasts (hDF, neonatal foreskin, ATCC PCS201010, American Type Culture Collection, Manassus, Va.) cells were seeded in each coated or control well at a density of 8,000-10,000 cells/well in 0.2 mL of fibroblast media (Fibroblast basal media, part PCS201030, American Type Culture Collection, Manassus, Va.), supplemented with 2% fetal bovine serum (Gibco/Thermofisher, Grand Island, N.Y.) and fibroblast growth kit (part PCS201040, American Type Culture Collection, Manassus, Va.), and were incubated at 37° C./5% $CO_2$ for at least 24 hours to promote cell attachment. Cells were then rinsed 3 times in D-PBS (pH 7.4) and incubated with 2 µM Calcein AM (Invitrogen, 4 mM stock solution in DMSO) in D-PBS for at least 30 minutes at room temperature.

Plates were read on a fluorescent plate reader (Molecular Devices SpectraMax M2, San Jose, Calif.) at 517 nm using an excitation wavelength of 494 nm. The coating experiment was then repeated for a total of n=16 wells per formulation, and the data were averaged. The table below shows the average fluorescence±the standard error due to hDF cells remaining attached to the passivating coating formulations, compared to control wells. All data was normalized to the control wells.

TABLE 2

| Polyurea | Cell Attachment via Calcein Staining Normalized to control uncoated well |
|---|---|
| Uncoated TCPS | 1.000 |
| Example 13 | 0.010 ± 0.003 |
| Example 31-d | −0.008 ± 0.005 |
| Example 31-e | 0.077 ± 0.008 |
| Example 31-f | −0.003 ± 0.004 |

The cells from each polyurea copolymer coating were also imaged with brightfield microscopy to qualitatively confirm the passivation level of the coatings by the relative number of adherent cells per well versus adherent cells in uncoated wells. The cell suspension of the supernatant of the coated wells can also be extracted, placed in a fresh 24 well tissue culture polystyrene plate, incubated for 24 hours at 37° C., then imaged with brightfield microscopy to determine if the coatings are cytotoxic.

Example 17. Photopolyurea Copolymer Synthesis

A polyurea copolymer containing benzophenone photoreactive group was synthesized as follows. 88.4 mg of 4,4'-diaminobenzophenone (0.45 mmole, Sigma Aldrich, St. Louis, Mo.) was dissolved in 30 ml of methanol with 168.6 mg of dipiperidyl propane (0.8 mmol, Sigma Aldrich, St. Louis, Mo.) and 1672.9 mg of Jeffamine™ ED 1900 (0.88 mmol, Sigma Aldrich, St. Louis, Mo.) at 60° C. overnight. The solution was then cooled to room temperature, and 445 mg of isophorone diisocyanate (2.0 mmole, Sigma Aldrich, St. Louis, Mo.) was added. The reaction mixture was stirred for 4 hours and was used without purification. The reaction mixture was diluted into deionized water to form a 10 mg/ml solution.

Example 18. Photopolyurea Copolymer Synthesis

A polyurea copolymer containing benzophenone photoreactive group was synthesized as follows. 88.6 mg of 4,4'-diaminobenzophenone (0.45 mmole, Sigma Aldrich, St. Louis, Mo.) was dissolved in 30 ml of methanol with 88.3 mg of dipiperidyl propane (0.42 mmole, Sigma Aldrich, St. Louis, Mo.) and 2406 mg of Jeffamine™ ED 1900 (1.3 mmole, Sigma Aldrich, St. Louis, Mo.) at 60° C. overnight. The solution was then cooled to room temperature, and 445 mg of isophorone diisocyanate (2.0 mmole Sigma Aldrich, St. Louis, Mo.) was added. The reaction mixture was stirred for 4 hours and was used without purification. The reaction mixture was diluted into deionized water to form a 10 mg/ml solution.

Example 19. Photopolyurea Copolymer Synthesis

A polyurea copolymer containing benzophenone photoreactive group was synthesized as follows. 22.9 mg of 4,4'-diaminobenzophenone (0.45 mmole, Sigma Aldrich, St. Louis, Mo.) was dissolved in a mixture of 5 ml of methanol and 10 ml of isopropanol. To this, 210 mg of dipiperidyl propane (1.0 mmole, Sigma Aldrich, St. Louis, Mo.) and 543.6 mg of Jeffamine™ ED 600 (0.9 mmole, Sigma Aldrich, St. Louis, Mo.) were added, and the solution was heated at 60° C. overnight. The solution was then cooled to room temperature, and 544 mg of isophorone diisocyanate (2.4 mmole, Sigma Aldrich, St. Louis, Mo.) was added. The reaction mixture was stirred for 4 hours and was used without purification. The reaction mixture was diluted into isopropanol to form a 10 mg/ml solution.

Example 20. Photopolyurea Copolymer Synthesis, Photo Terminated

A polyurea copolymer containing benzophenone photoreactive end group is synthesized as follows. 8 mg of 4-aminobenzophenone (40 umol, Sigma Aldrich, St. Louis, Mo.) is dissolved in 15 ml of isopropanol, to which 185 mg of dipiperidyl propane (0.88 mmole, Sigma Aldrich, St. Louis, Mo.) and 52.8 mg of Jeffamine™ ED600 (0.88 mmol Sigma Aldrich, St. Louis, Mo.) is added. After all the amines dissolve, 0.42 ml of isophorone diisocyanate (2 mmol, Sigma Aldrich, St. Louis, Mo.) is added via syringe and the reaction mixture stirs at room temperature for 2 hours. The benzophenone-terminated polyurea can be used without further purification.

Example 21. Polyurea Copolymer Synthesis, Biotin Terminated

A polyurea copolymer containing terminal biomolecule moieties was prepared as follows. 13 mg of neurobiotin (40 umol, Vector Laboratories, Burlingame, Calif.) was dissolved in 15 ml of isopropanol, to which 208.6 mg of dipiperidyl propane (0.98 mmole, Sigma Aldrich, St. Louis, Mo.) and 19623 mg of Jeffamine™ ED1900 (0.98 mmol Sigma Aldrich, St. Louis, Mo.) was added. After all the amines dissolved, 0.42 ml of isophorone diisocyanate (2 mmol, Sigma Aldrich, St. Louis, Mo.) was added via syringe, and the reaction mixture stirred at room temperature for 2 hours. The biotin-terminated polyurea was dialyzed against deionized water for purification.

Example 22. Photopolyurea Copolymer Synthesis, Biotin Terminated

A polyurea copolymer containing photoreactive groups and terminal biomolecule moieties is prepared as follows. 43.2 mg of 4,4'-diaminobenzophenone (0.22 mmole, Sigma Aldrich, St. Louis, Mo.) is dissolved in 30 ml of methanol with 13 mg of neurobiotin (40 umol, Vector Laboratories, Burlingame, Calif.), 139 mg of dipiperidyl propane (0.66 mmole, Sigma Aldrich, St. Louis, Mo.) and 1672 mg of Jeffamine™ ED1900 (0.88 mmol Sigma Aldrich, St. Louis, Mo.) added. After all the amines dissolve, 0.42 ml of isophorone diisocyanate (2 mmol, Sigma Aldrich, St. Louis, Mo.) is added via syringe, and the reaction mixture stirs at room temperature for 2 hours. The biotin-terminated photopolyurea can be dialyzed against deionized water for purification if desired or diluted to 10 mg/ml in water without purification.

Example 23. Photopolyurea-HA Copolymer Synthesis

A polyurea copolymer containing photoreactive groups and terminal biomolecule moieties was prepared as follows. 2.5 grams of 2 mg/ml hyaluronic acid (Lifecore, Chaska, Minn.) in 50 uM IVIES buffer was activated by adding 10.4 mg of N-(3-dimethylaminopropyl)-N'-ethylcarbodiimide hydrochloride (EDC, Sigma Aldrich, St. Louis, Mo.) and 7.4 mg N-hydroxysulfosuccinimide sodium salt (sulfo-NHS, Sigma Aldrich, St. Louis, Mo.) and coupling with 2.0 grams of a 50 mg/ml aqueous solution of photopolyurea (as prepared in Example 17) mixed on an orbital shaker at 150 rpm overnight at room temperature. The reaction was protected from incident light. The photo-derivatized hyaluronic acid was purified by dialysis with 12-14K dialysis tubing (Spectrum Labs, Rancho Dominguez, Calif.) against deionized water. Thin layer chromatography with 90:10 chloroform: methanol as eluent showed that the hyaluronic acid was UV active, indicating successful coupling.

Example 24. Photopolyurea-Streptavidin Copolymer Synthesis

A polyurea copolymer containing photoreactive group and biomolecule moieties is prepared as follows. 100 mg of streptavidin (Sigma Aldrich, St. Louis, Mo.) is activated by dissolving at 1 mg/ml in 0.05 MES buffer. To this 100 ml solution, 0.11 grams of N-hydroxysulfosuccinimide sodium salt (sulfo-NHS, Sigma Aldrich, St. Louis, Mo.) and 0.038 grams N-(3-dimethylaminopropyl)-N'-ethylcarbodiimide hydrochloride (EDC, Sigma Aldrich, St. Louis, Mo.) are added and stirred for 15 minutes at room temperature. To this reaction mixture, a solution of 200 mg of photopolyurea prepared as in Example 17 in 20 ml of 0.1M sodium phosphate buffer (pH 7.5) is added, and the reaction mixture is stirred at room temperature for 2 hours. The photo-derivatized streptavidin is purified by dialysis or gel filtration.

Example 25. FITC Polyurea Copolymer Synthesis

A polyurea copolymer containing fluorescent dye was synthesized as follows. 79 mg of fluorescein isothiocyanate (FITC, 0.2 mmole, Sigma Aldrich, St. Louis, Mo.) was dissolved in 5 ml of isopropanol. A solution of 210.0 mg dipiperidyl propane (1.0 mmol, Sigma Aldrich, St. Louis, Mo.) and 2006.2 mg Jeffamine™ ED1900 (1.0 mmol, Sigma Aldrich, St. Louis, Mo.) in 12 ml of isopropanol was added to the FITC solution and stirred at room temperature for two hours. After two hours, 445 mg of isophorone diisocyanate (2.0 mmol, Sigma Aldrich, St. Louis, Mo.) was added via syringe and the reaction mixture stirred at room temperature for two days until the residual isocyanate was undetectable by FTIR.

Example 26. Photopolyurea Copolymer Synthesis

A polyurea copolymer containing benzophenone photoreactive group was synthesized as follows. 4.5 mg of 4,4'-diaminobenzophenone (0.02 mmole, Sigma Aldrich, St. Louis, Mo.) was dissolved in 15 ml of methanol with 212.4 mg of dipiperidyl propane (1.0 mmol, Sigma Aldrich, St. Louis, Mo.) and 2002.1 mg of Jeffamine™ ED 1900 (1.0 mmol, Sigma Aldrich, St. Louis, Mo.) at 60° C. overnight. The solution was then cooled to room temperature and 544 mg of isophorone diisocyanate (2.4 mmole, Sigma Aldrich, St. Louis, Mo.) was added. The reaction mixture was stirred for 2 days at room temperature and was used without purification. The reaction mixture was diluted into 1×phosphate buffered saline (PBS, Gibco/ThermoFisher, Grand Island, N.Y.) to form a solution at 10 mg/ml solution without precipitation.

Example 27. Photopolyurea Copolymer Synthesis

A polyurea copolymer containing benzophenone photoreactive group was synthesized as follows. 42.9 mg of 4,4'-diaminobenzophenone (0.2 mmole, Sigma Aldrich, St. Louis, Mo.) was dissolved in 15 ml of methanol at 60° C.

overnight. To this solution, 127.4 mg of dipiperidyl propane (0.6 mmol, Sigma Aldrich, St. Louis, Mo.) and 2395.1 mg of Jeffamine™ ED1900 (1.2 mmole, Sigma Aldrich, St. Louis, Mo.) were added, followed by 544 mg of isophorone diisocyanate (2.4 mmole, Sigma Aldrich, St. Louis, Mo.) added via syringe. The reaction mixture was stirred for 2 days at room temperature and was used without purification. No precipitation occurred. The reaction mixture was diluted into 1×phosphate buffered saline (PBS, Gibco/ThermoFisher, Grand Island, N.Y.) to form a solution at 10 mg/ml solution without precipitation.

Example 28. Passivation by Photopolyurea Copolymers

Microwells in a 96-well plate were coated by physisorption as follows. 100 uL of a 10 mg/ml solution of the photo-derivatized polyurea copolymers prepared as described in Example 27, Example 26, or 1×PBS (control) were added to four wells each of a 96 well plate. This microwell plate with the photopolyurea copolymer blocking solutions in the wells was orbitally shaken for 1 hour while protected from light. After 1 hour, the solutions were removed and the wells were rinsed three times with 1×PBS solution. To each well, 50 uL of a 1:10,000 dilution of rabbit anti-mouse IgG-horseradish peroxidase (Sigma Aldrich, St. Louis, Mo.) in PBS was added. The 96 well plate was then orbitally shaken at room temperature in the dark for one hour. After one hour, the wells were all rinsed twice with PBS, the plate was inverted to remove any remaining solution, then 50 ul/well of TMB developing solution (KPL/Seracare, Milford, Mass.) was added and the plate was orbitally shaken at room temperature in the dark for 10 minutes. After 10 minutes, 50 ul/well of 0.5N sulfuric acid was added to stop the reaction, and the optical density of the solutions in each well was measured at 450 nm. Results of the experiment were reported and averaged:

TABLE 3

| Sample | Abs 450 nm | | | | |
| --- | --- | --- | --- | --- | --- |
| | Well 1 | Well 2 | Well 3 | Well 4 | Average ± standard deviation |
| Photopolyurea (Example 27) | 0.017 | 0.022 | 0.010 | 0.010 | 0.0148 ± 0.006 |
| Photopolyurea (Example 26) | 0.018 | 0.027 | 0.034 | 0.027 | 0.0265 ± 0.007 |
| PBS control | 1.985 | 1.930 | 2.002 | 1.787 | 1.926 ± 0.098 |

Results showed passivation of the microwell surface with photo-derivatized polyurea copolymers prepared in accordance with inventive principles.

Example 29. Photopolyurea Copolymer Synthesis

A polyurea copolymer containing benzophenone photoreactive group was synthesized as follows. 42 mg of 4,4'-diaminobenzophenone (0.2 mmole, Sigma Aldrich, St. Louis, Mo.) was dissolved in 5 ml of methanol at 60° C. overnight, then a solution of 182.1 mg of dipiperidyl propane (0.9 mmol, Sigma Aldrich, St. Louis, Mo.) and 558.1 mg of Jeffamine™ ED 600 (0.9 mmol, Sigma Aldrich, St. Louis, Mo.) in 10 ml of isopropanol was added to the methanol solution after it cooled. To this 2:1 isopropanol: methanol diamine solution, 544 mg of isophorone diisocyanate (2.4 mmole, Sigma Aldrich, St. Louis, Mo.) was added by syringe. The reaction mixture stirred for 2 hours at room temperature and was used without purification. Reaction product did not precipitate but remained in solution.

Example 30. Photopolyurea Copolymer Coating on Polyurethane Rod

A coating solution was made up of 42 ml of 50 mg/ml polyvinylpyrrolidone (BASF, Germany) in isopropanol, 5 ml of the solution prepared in Example 29, and 3 ml of isopropanol. The overall total dissolved solids of the coating solution were 6.0%. This solution was dipcoated onto polyurethane rod (¼ inch diameter, McMaster Carr, Elmhurst, Ill.) that had been pre-cleaned with isopropanol wiping. The rods were dipped into the coating solution, dwelled 30 seconds, then extracted at 1 cm/sec and air dried for 10 minutes. The rods were UV cured for 5 minutes with 254 nm light. The coating was stained with a 0.35% aqueous solution of Congo Red dye. Repeated rubbing with gloved fingers did not remove the coating. Uncured coatings or polyvinylpyrrolidone without crosslinking can be removed by simple rub; therefore, the photogroups were active in the photopolyurea. Results demonstrated durability of photo-derivatized polyurea copolymer prepared in accordance with inventive principles.

Example 31. Durometer Testing of Polyurea Copolymers

A variety of polyurea copolymers were synthesized and tested for hardness as follows. Polyurea copolymers were synthesized by combining X grams of Jeffamine™ ED1900 (Sigma Aldrich, Milwaukee, Wis.) and Y grams of dipiperidyl propane (Sigma Aldrich, Milwaukee, Wis.) with Z grams of isophorone diisocyanate (Sigma Aldrich, Milwaukee, Wis.) in 15 ml of isopropanol, where X, Y, and Z are described in the table below. Each reaction mixture was stirred vigorously at room temperature for 24 hours, then used without further purification. The resulting products were each soluble in isopropanol.

Each solution was then cast out of the isopropanol reaction solvent onto a glass pan and dried at room temperature to evaporate the solvent. The resulting films were at least 0.25 inches thick. Films were tested for hardness with a digital Shore D durometer (Phase II model PHT-980, Phase II, Upper Saddle River, N.J.) with at least three measurements. The average durometer in Shore D is recorded in the table below.

TABLE 4

| Example | X grams of Jeffamine ED 1900 | Y grams of dipiperidyl propane | Z grams of isophorone diisocyanate | Shore D hardness |
| --- | --- | --- | --- | --- |
| 13 | | See example 13 | | 17D |
| 15 | | See example 15 | | 13D |
| 31-c | 16.01 | 0.4255 | 2.6229 | 5D |
| 31-d | 4.0011 | 1.6814 | 2.2882 | 25D |
| 31-e | 13.05 | 0.2485 | 2.6810 | 4D |
| 31-f | 11.03 | 0.9493 | 2.6803 | 8D |
| 31-6 | 0.8475 | 0.1260 | 0.5109 | 19D |

Example 32. Materials Properties of Polyurea Copolymers

The polyurea copolymers from Example 13 and Example 31-d were each cast as films directly out of their respective isopropanol reaction solvent onto two separate glass pans. After evaporation of the solvent, dogbone-shaped samples were cut out of each film with a standardized die. The films were characterized on an Instron Universal Tester 3343 (Instron, Norwood Mass.) by elongating the sample until break at a rate of 1 mm/sec while measuring the force to generate stress-strain curves. From the curve, the Young's modulus and tensile strength were calculated as shown in the table below.

TABLE 5

| Sample | Young's modulus in psi | Tensile strength in psi | Appearance/ feel to touch |
|---|---|---|---|
| Polyurea copolymer from Example 13 | 3947 | 1139 | Smooth clear, non-tacky film |
| Polyurea copolymer from Example 31-d | 51086 | 3563 | Smooth clear, non-tacky film |

Example 33. Bacterial Adherence Testing of Polyurea Copolymers

Acrylic slides (Ted Pella, Inc. Redding, Calif.) were cleaned by wiping three times with isopropanol, air dried, and then dip coated with a 10 mg/ml solution of either the polyurea copolymer prepared in Example 1 or in Example 31-f in isopropanol. The slides remained in the coating solution for 30 seconds and then were extracted at a rate of 0.5 cm/sec. The coated slides were air dried for 15 minutes, and then illuminated for 2 minutes per side with UVB (306 nm) light to sterilize them.

The coated sterilized slides were then each placed in 10 ml of $E.\ Coli$ (DH5a, ATCC, Manassus, Va.) in Luria-Bertani (LB) broth (MP Biomedical, Solon, Ohio, freshly seeded overnight and grown at 37° C., 100 rpm, with an OD adjusted to 0.5). The coated slides remained in the $E.\ Coli$ solution overnight at 37° C., 100 rpm. After the $E.\ Coli$ exposure, the slides were rinsed three times with 13 ml each of Butterfield's buffer for five minutes each.

The rinsed slides were stained with 2 ml of safranin dye (1:5 concentration, PML Microbiologicals, Wilsonville, Oreg.) for one minute, then rinsed with 2 ml of Butterfield's buffer for one minute. Slides were visualized by microscope (Leica, Buffalo Grove, Ill.) at 50× with a wet mount and ImageJ used to count the number of cells. At least six images per slide were taken and the number of bacteria per $mm^2$ averaged with one standard deviation reported in the table below.

TABLE 6

| Coating | $E.\ Coli$ bacteria/$mm^2$ Average ± standard deviation |
|---|---|
| Uncoated Acrylic Slide | 1089 ± 1039 |
| Acrylic slide coated with Example 31-f | 207 ± 227 |
| Acrylic slide coated with Example 1 | 516 ± 491 |

Example 34. Molecular Weight of Polyurea Copolymers Controlled by Monomer Ratios The molecular weight of a polyurea copolymer can be controlled by the feed ratio of monomers. To demonstrate this effect, the polyurea copolymer from Example 13 was prepared using the same procedure but with different feed ratios as detailed in the table below. Additionally, the reaction was run under slightly more dilute conditions (30 ml of isopropanol solvent vs 15 ml), which can reduce molecular weight, and with a quench reagent present.

The resulting polyurea copolymer solutions were analyzed without purification by diluting to 3 mg/ml in tetrahydrofuran, filtering through a 0.20 micron filter and injecting 50 µL onto a gel permeation system (Agilent 1200 GPC with two PLGel 5.0 µm Mixed C columns (250×10 mm each) Agilent Technologies, Santa Clara, Calif.) at 45° C. with a flow rate of 1.2 mL/min using tetrahydrofuran as eluent. The polyurea copolymers were detected with a refractive index detector and analyzed against a set of 12 polystyrene standards (Agilent Easi-Cal standards: 6.035M, 3.039M, 990.5K, 508K, 184.9K, 74.8K, 21.72K, 6180, 2590, 1370, 580, 162, Agilent Technologies, Santa Clara, Calif.).

TABLE 7

| Sample | mL of isophorone diisocyanate | Grams of Jeffamine ED 1900 | Grams of dipiperidyl propane | Theoretical ratio of total diisocyanate: total diamine* | Reaction Solvent in mL | Mw |
|---|---|---|---|---|---|---|
| 34-a | 0.50 mL | 2.0061 | 0.2112 | 1.2:1 | 15 ml IPA | 19,299 |
| 34-b | 0.42 mL | 2.0284 | 0.2138 | 1:1 | 30 ml IPA | 45,265 |
| 34-c | 0.42 mL | 2.0053 | 0.2141 | 1:1 | 15 mL IPA | 50,275 |
| 34-d | 0.40 mL | 2.0004 | 0.2131 | 0.95:1 | 15 mL IPA | 62,799 |
| 34-e | 0.38 mL | 2.0077 | 0.2135 | 0.9:1 | 15 mL IPA | 38,814 |
| 34-f | 0.29 mL | 1.0008 | 0.1041 | 1.35:1 | 8 ml IPA, 1 ml methanol added after 18 hours reaction | 25,669 |
| 34-g | 0.29 mL | 1.0044 | 0.1041 | 1.35:1 | 8 ml IPA, 1 ml water added after 18 hours reaction | 18,426 |

*note the theoretical ratio may differ from the actual ratio if the polyethylene glycol diamine is not 100% functionalized on the terminus or alternately if the isocyanate has reacted prior to use.

Example 35. Effect of Ratio on Polyurea Aqueous Solubility

The ratio of the total isocyanates:total amines can affect the solubility of a polyurea copolymer. Polyurea copolymers with a higher PEG ratio are less affected than lower PEG ratio. To demonstrate this effect, the polyurea copolymer from Example 13 was prepared using the same procedure but with different feed ratios as detailed in the table below.

TABLE 8

| Sample | mL of isophorone diisocyanate | Grams of Jeffamine ED 1900 | Grams of dipiperidyl propane | Theoretical ratio of total diisocyanate: total diamine | Molar ratio of PEG: Dipiperidyl propane | Solubility at 10 mg/ml water |
|---|---|---|---|---|---|---|
| 35-a | 0.285 mL | 0.8047 | 0.1268 | 1.3:1 | 40:60 | Soluble |
| 35-b | 0.34 mL | 1.6017 | 0.2508 | 1:1 | 40:60 | Not soluble |
| 34-a | 0.50 mL | 2.0061 | 0.2112 | 1.2:1 | 50:50 | Soluble |
| 34-c | 0.42 mL | 2.0053 | 0.2141 | 1:1 | 50:50 | Soluble |

The invention claimed is:

1. A coating composition for a surface of a medical device, the coating composition comprising a polyurea copolymer having a polymer backbone and comprising a reaction product of:
  (a) a diamine composition comprising a polyethylene glycol diamine compound having a formula (I), (II), or a combination of (I) and (II):

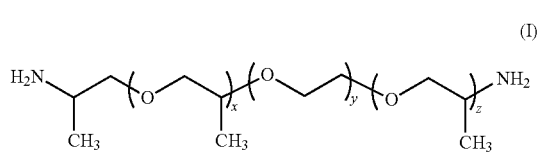

(I)

wherein y is an integer in the range of 2 to 40, and x+z is an integer in the range of 1 to 8; or

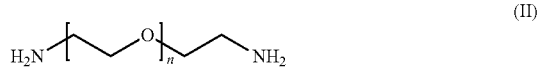

(II)

wherein n is an integer in the range of 1 to 500; and
  (b) a diisocyanate, wherein the diisocyanate is present in a molar ratio with total diamines in (a) in a range of 2:1 to 1:2.

2. The coating composition of claim 1 wherein the polyethylene glycol diamine compound has a molecular weight of 500 to 2500.

3. The coating composition of claim 1 wherein the di amine composition of (a) comprises a polyethylene glycol diamine compound in an amount in a range of 20 to 99 molar percent, and a dipiperidyl alkane in an amount in a range of 0.1 to 80 molar percent of the diamine composition.

4. The coating composition of claim 3 wherein the dipiperidyl alkane comprises one or more of dipiperidyl propane, dipiperidyl methane, dipiperidyl ethane, dipiperidyl butane, dipiperidyl pentane, dipiperidyl hexane, dipiperidyl heptane, and dipiperidyl octane, or bipiperidine.

5. The coating composition of claim 1 wherein the diisocyanate has a formula:

where B is a bivalent alkyl radical having 2 to 20 carbon atoms.

6. The coating composition of claim 5, wherein the diisocyanate is selected from hexane diisocyanate and isophorone diisocyanate.

7. The coating composition of claim 1 wherein the copolymer comprises polyethylene glycol groups in amount of 25 to 95 weight percent, based on total weight of the polyurea copolymer.

8. The coating composition of claim 1 having a Hardness Value of 30D or less.

9. The coating composition of claim 1 wherein the polyurea copolymer has an average molecular weight of 100,000 or less.

10. The coating composition of claim 1 wherein the polyurea copolymer has a Young's modulus that is at least 1,000 psi.

11. The coating composition of claim 1 wherein the polyurea copolymer further comprises one or more latent reactive groups selected from photoreactive groups, thermally reactive groups, chemically reactive groups, or a combination of any two or more of these.

12. The coating composition of claim 1 wherein the copolymer does not include silane or siloxane.

13. The coating composition of claim 1 further comprising a solvent selected from water, alcohol, an alcohol-water mixture, or a buffer, wherein the polyurea copolymer is in solution.

14. The composition of claim 13 comprising a total solids content of 10% or lower.

15. An article comprising a medical device having a surface containing a passivating coating, the passivating coating comprising a polyurea copolymer that is a reaction product of:
  (a) a diamine composition comprising a polyethylene glycol diamine compound having a formula (I), (II), or a mixture of (I) and (II):

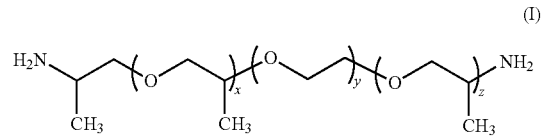

(I)

wherein y is an integer in the range of 2 to 40, and x+z is an integer in the range of 1 to 8; or

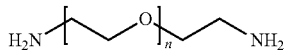

(II)

wherein n is an integer in the range of 1 to 500; and (b) a diisocyanate, wherein the diisocyanate is present in a molar ratio with total diamines in (a) in a range of 2:1 to 1:2.

16. The article of claim 15, wherein the passivating coating has a Hardness Value of 30D or less.

17. The article of claim 15, wherein the polyurea copolymer has an average molecular weight of 100,000 or less.

18. The article of claim 15, wherein the passivating coating has a Young's modulus that is at least 1,000 psi.

19. The article of claim 15, wherein the passivating coating has a thickness of 10 microns or less.

20. The article of claim 15, wherein the medical device is an implantable medical device, a medical device for temporary insertion into a patient's body, a device that contacts biological fluids outside a patient's body, or an in vitro diagnostic device.

21. The article of claim 20 wherein the medical device is selected from cell culture ware selected from flasks, plates, tubes, and vials; magnetic micro- and nanoparticles; polystyrene micro- and nanoparticles; metallic micro- and nanoparticles; microwell plates; slides; membranes; tubing; gels; petri dishes; bioreactors; catheters; guidewires; introducers; and sensor surfaces.

22. The article of claim 15 wherein the surface comprises metal, polymer, ceramic, glass, fabric, or biomaterial.

23. The article of claim 15, wherein the polyurea copolymer further comprises one or more latent reactive groups selected from photoreactive groups, thermally, reactive groups, chemically reactive groups, or a combination on any two or more of these.

24. The coating composition of claim 1 wherein the surface comprises metal, polymer, ceramic, glass, fabric, or biomaterial.

25. The coating composition of claim 1, wherein the polyurea copolymer further comprises one or more latent reactive groups selected from photoreactive groups, thermally reactive groups, chemically reactive groups, or a combination on any two or more of these.

26. The coating composition of claim 1, wherein the medical device is selected from cell culture ware selected from flasks, plates, tubes, and vials; magnetic micro- and nanoparticles; polystyrene micro- and nanoparticles; metallic micro- and nanoparticles; microwell plates; slides; membranes; tubing; gels; petri dishes; bioreactors; catheters; guidewires; introducers; and sensor surfaces.

* * * * *